(12) United States Patent
Aklog et al.

(10) Patent No.: US 10,434,296 B2
(45) Date of Patent: Oct. 8, 2019

(54) INTRAOSSEOUS INFUSION PORTS AND METHODS OF USE

(71) Applicant: PAVmed Inc., New York, NY (US)

(72) Inventors: Lishan Aklog, New York, NY (US); Brian J. deGuzman, Paradise Valley, AZ (US); Mark J. Orphanos, Foxboro, MA (US)

(73) Assignee: PAVmed Inc., New York, NY (US)

( * ) Notice: Subject to any disclaimer, the term of this patent is extended or adjusted under 35 U.S.C. 154(b) by 0 days.

(21) Appl. No.: 15/964,292

(22) Filed: Apr. 27, 2018

(65) Prior Publication Data
US 2018/0256869 A1    Sep. 13, 2018

Related U.S. Application Data

(62) Division of application No. 14/940,889, filed on Nov. 13, 2015.
(Continued)

(51) Int. Cl.
*A61M 39/02*    (2006.01)
*A61M 1/36*    (2006.01)

(52) U.S. Cl.
CPC .......... *A61M 39/02* (2013.01); *A61M 1/3655* (2013.01); *A61M 2039/0205* (2013.01);
(Continued)

(58) Field of Classification Search
CPC ................ A61M 39/02; A61M 1/3655; A61M 2039/027; A61M 2039/0261;
(Continued)

(56) References Cited

U.S. PATENT DOCUMENTS 4,772,261 A    9/1988   Von Hoff et al.
5,122,114 A    6/1992   Miller et al.
(Continued)

FOREIGN PATENT DOCUMENTS

WO    1990000412 A1    1/1990
WO    92/13591 A2      8/1992
(Continued)

OTHER PUBLICATIONS

PCT International Search Report and Written Opinion Issued in International Application No. PCT/US2015/060669 dated Jan. 29, 2016.
(Continued)

*Primary Examiner* — Amber R Stiles
(74) *Attorney, Agent, or Firm* — Greenberg Traurig, LLP; Chinh H. Pham; Brian J. Assessor

(57) ABSTRACT

Example embodiments are related to intraosseous infusion port (IOP) devices to provide access to bone marrow cavities. The IOP device according to example embodiments may comprise a proximal portion with a hollow chamber extending through the proximal portion, the hollow chamber having a proximal inlet for receiving an insertion device. The IOP device may also include an anchor portion positioned distally to the proximal portion, the anchor portion may be configured for anchoring the infusion port device in a bone, and an open-ended channel extending through the anchor portion, the channel being in fluid communication with the hollow chamber, such that, when the infusion port is implanted into a bone, the channel and the hollow chamber create a substantially straight pathway terminating at an opening at its distal end for insertion of the insertion device towards the bone marrow.

11 Claims, 49 Drawing Sheets

Related U.S. Application Data

(60) Provisional application No. 62/079,266, filed on Nov. 13, 2014.

(52) U.S. Cl.
CPC . *A61M 2039/025* (2013.01); *A61M 2039/027* (2013.01); *A61M 2039/0258* (2013.01); *A61M 2039/0261* (2013.01)

(58) Field of Classification Search
CPC .. A61M 2039/0258; A61M 2039/0205; A61M 2039/025
See application file for complete search history.

(56) References Cited

U.S. PATENT DOCUMENTS

| | | | |
|---|---|---|---|
| 5,332,398 A * | 7/1994 | Miller | A61M 39/0208 604/175 |
| 5,456,267 A | 10/1995 | Stark | |
| 5,817,052 A | 10/1998 | Johnson et al. | |
| 5,824,087 A | 10/1998 | Aspden et al. | |
| 5,868,711 A | 2/1999 | Kramer et al. | |
| 6,018,094 A | 1/2000 | Fox | |
| 6,761,726 B1 | 7/2004 | Findlay et al. | |
| 6,887,246 B2 | 5/2005 | Bhatnagar et al. | |
| 7,811,260 B2 | 10/2010 | Miller et al. | |
| 7,815,642 B2 | 10/2010 | Miller | |
| 8,062,270 B2 | 11/2011 | Sweeney | |
| 8,142,365 B2 | 3/2012 | Miller | |
| 8,308,693 B2 | 11/2012 | Miller et al. | |
| 8,348,956 B2 | 1/2013 | Rabiner | |
| 8,419,683 B2 | 4/2013 | Miller et al. | |
| 8,486,027 B2 | 7/2013 | Findlay et al. | |
| 8,506,568 B2 | 8/2013 | Miller | |
| 8,641,715 B2 | 2/2014 | Miller | |
| 8,690,791 B2 | 4/2014 | Miller | |
| 8,870,872 B2 | 10/2014 | Miller | |
| 8,876,826 B2 | 11/2014 | Miller | |
| 8,992,535 B2 | 3/2015 | Miller | |
| 8,998,848 B2 | 4/2015 | Miller et al. | |
| 2003/0036763 A1 | 2/2003 | Bhatnagar et al. | |
| 2004/0127905 A1 | 7/2004 | Lim et al. | |
| 2005/0148940 A1 | 7/2005 | Miller | |
| 2005/0251144 A1 * | 11/2005 | Wilson | A61B 5/031 606/108 |
| 2005/0026759 A1 | 12/2005 | Ricci et al. | |
| 2006/0015006 A1 | 1/2006 | Turieo et al. | |
| 2006/0167378 A1 | 7/2006 | Miller | |
| 2007/0084742 A1 | 4/2007 | Miller et al. | |
| 2008/0065083 A1 * | 3/2008 | Truckai | A61B 17/3472 600/407 |
| 2009/0137899 A1 | 5/2009 | Bengtson | |
| 2009/0312764 A1 | 12/2009 | Marino | |
| 2009/0312782 A1 | 12/2009 | Park | |
| 2011/0004163 A1 | 1/2011 | Vaidya | |
| 2011/0076640 A1 * | 3/2011 | Jones | A61B 17/3472 433/89 |
| 2011/0082387 A1 | 4/2011 | Miller et al. | |
| 2011/0098604 A1 | 4/2011 | Miller | |
| 2011/0152866 A1 | 6/2011 | Knutson | |
| 2012/0059349 A1 * | 3/2012 | Kuo | A61M 5/1407 604/500 |
| 2012/0095440 A1 | 4/2012 | Islam | |
| 2012/0109061 A1 | 5/2012 | Miller et al. | |
| 2013/0102924 A1 | 4/2013 | Findlay et al. | |
| 2015/0314118 A1 * | 11/2015 | Kelekis | A61M 39/02 604/502 |

FOREIGN PATENT DOCUMENTS

| | | |
|---|---|---|
| WO | 2013/003885 | 1/2013 |
| WO | 2016057090 A1 | 4/2016 |

OTHER PUBLICATIONS

U.S. Appl. No. 14/940,889, 2016-0136410, filed Nov. 13, 2015, May 19, 2016, Intraosseous Infusion Ports and Methods of Use.
Supplementary European Search Report for corresponding European Patent Application No. 15859903.5 dated Aug. 13, 2018.
Non-Final Office Action in corresponding U.S. Appl. No. 14/940,889, dated Mar. 7, 2019.

* cited by examiner

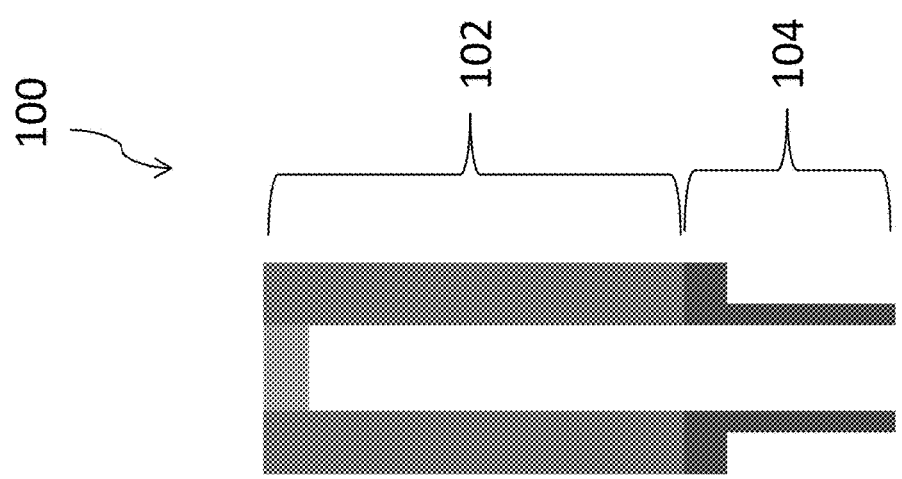

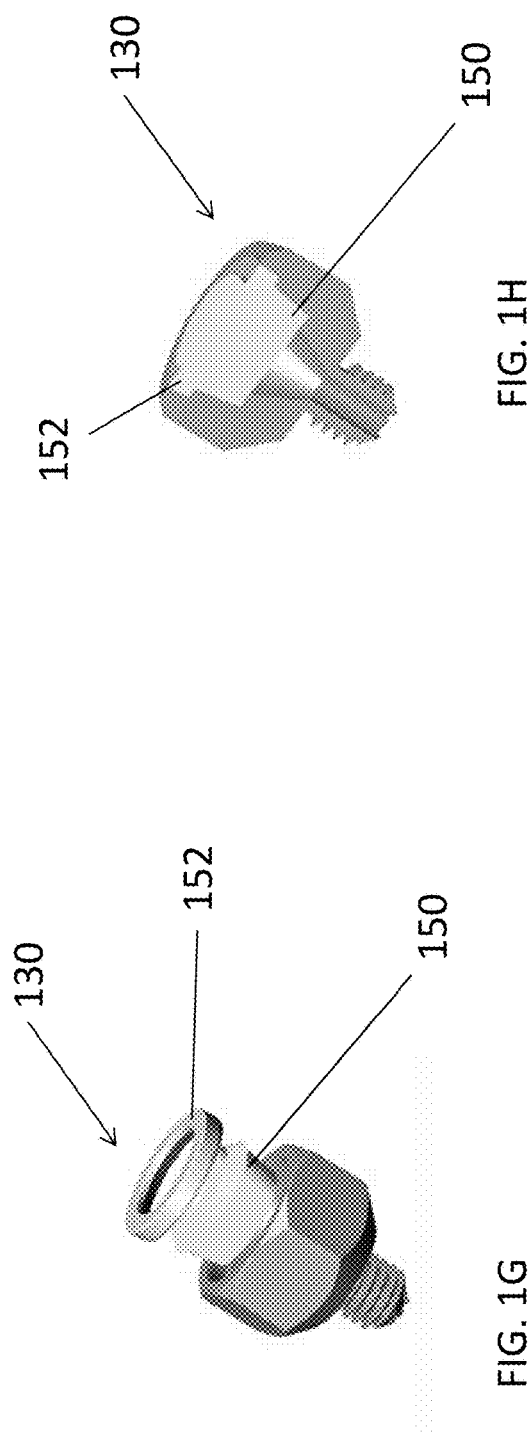
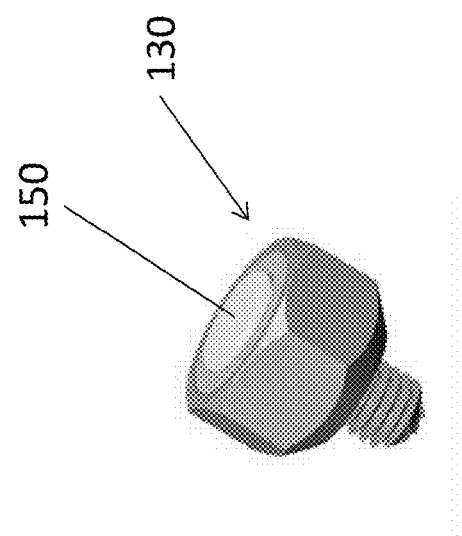
FIG. 1H
FIG. 1I
FIG. 1G

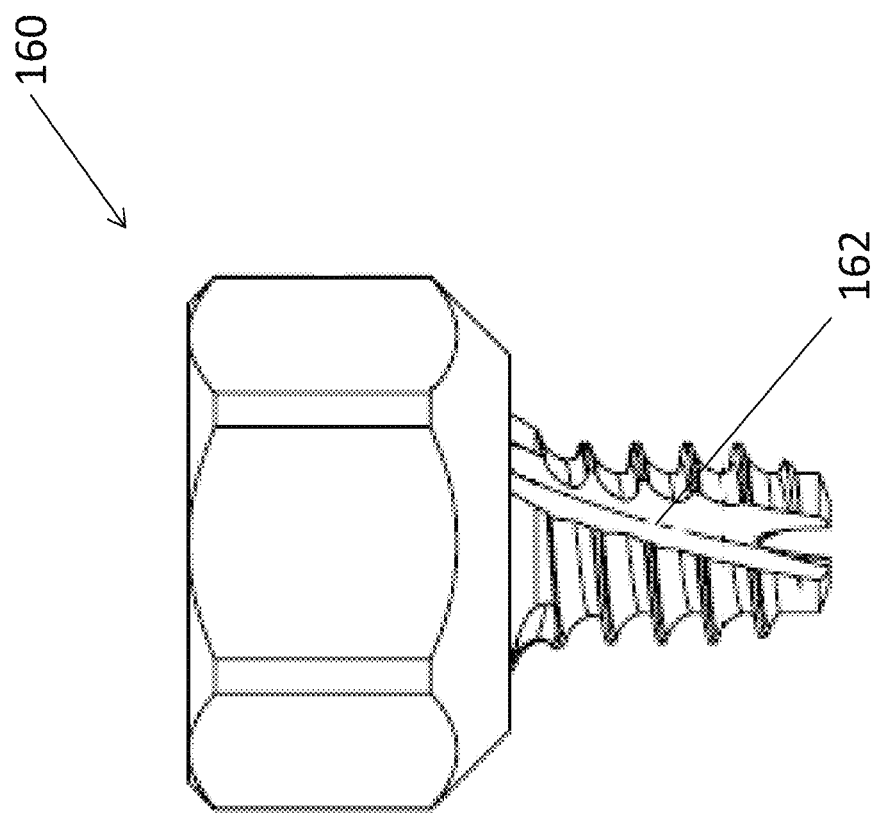

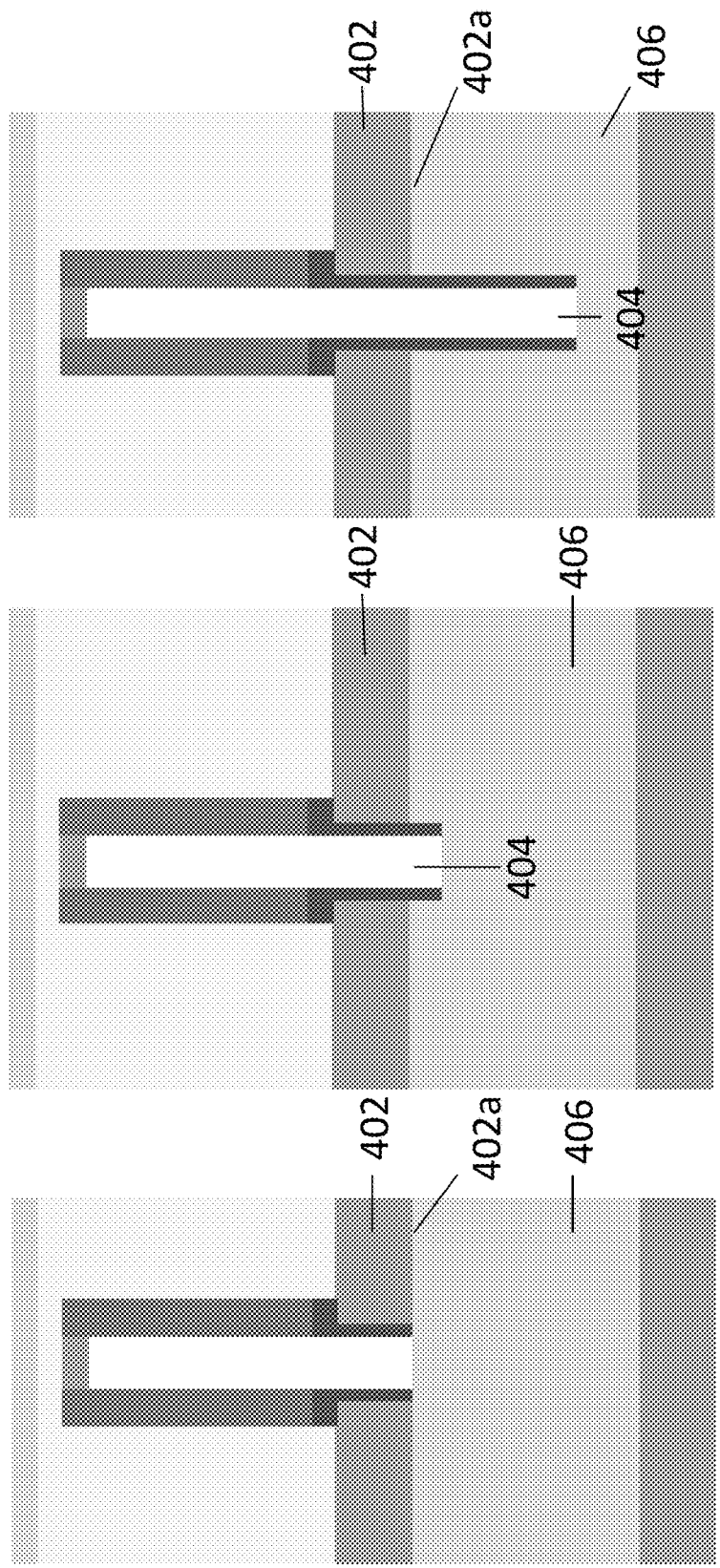

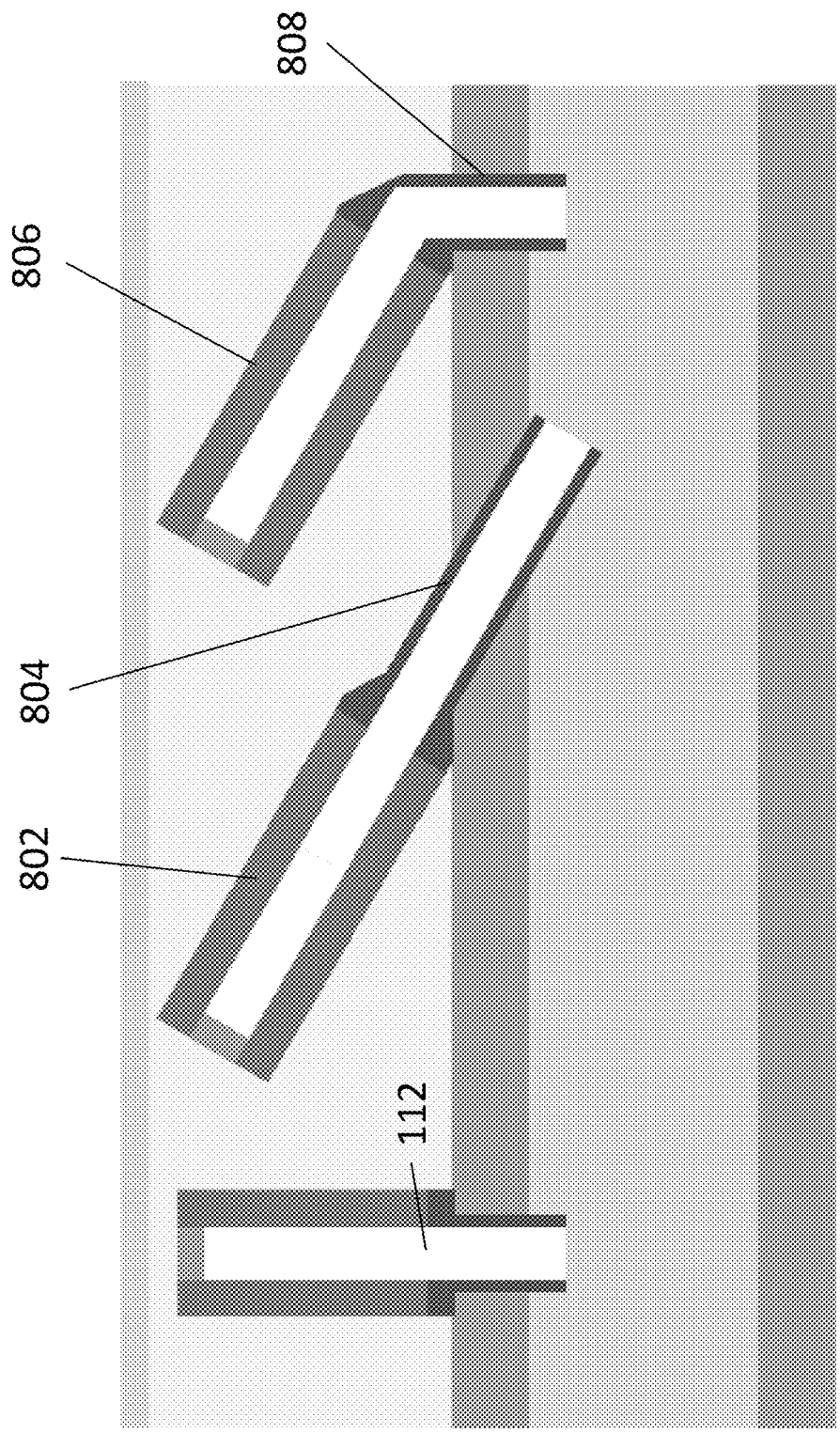

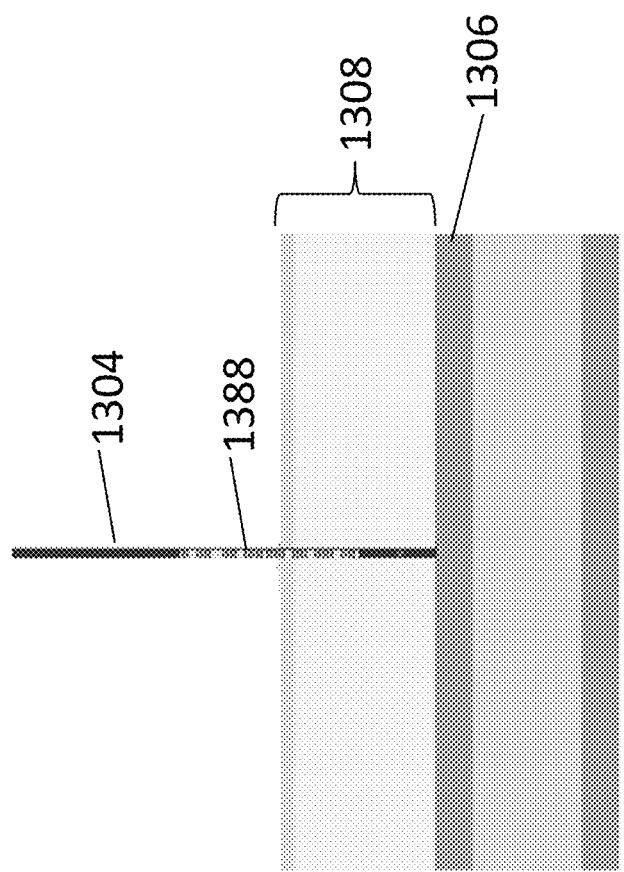

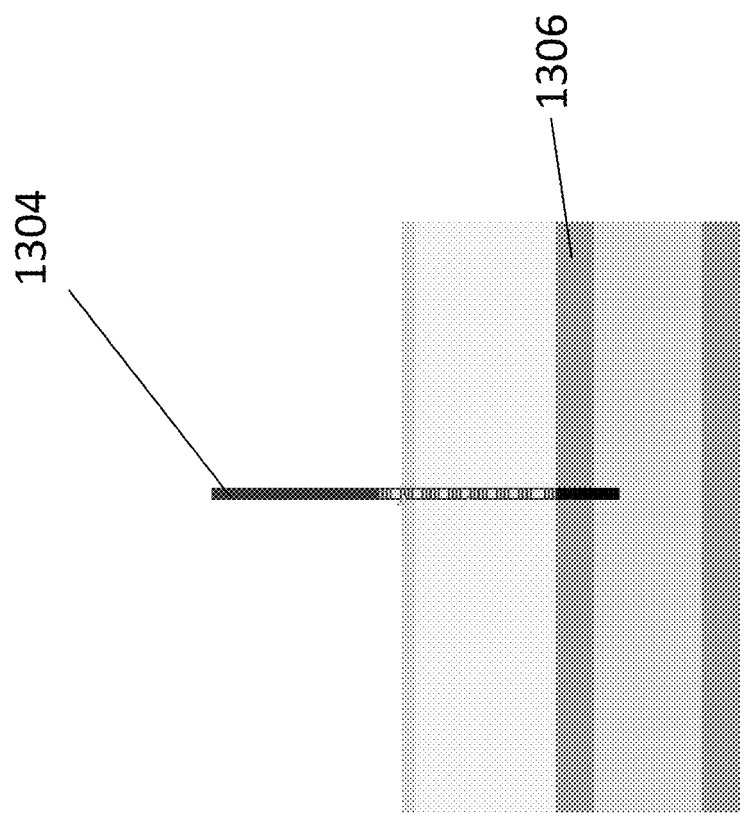

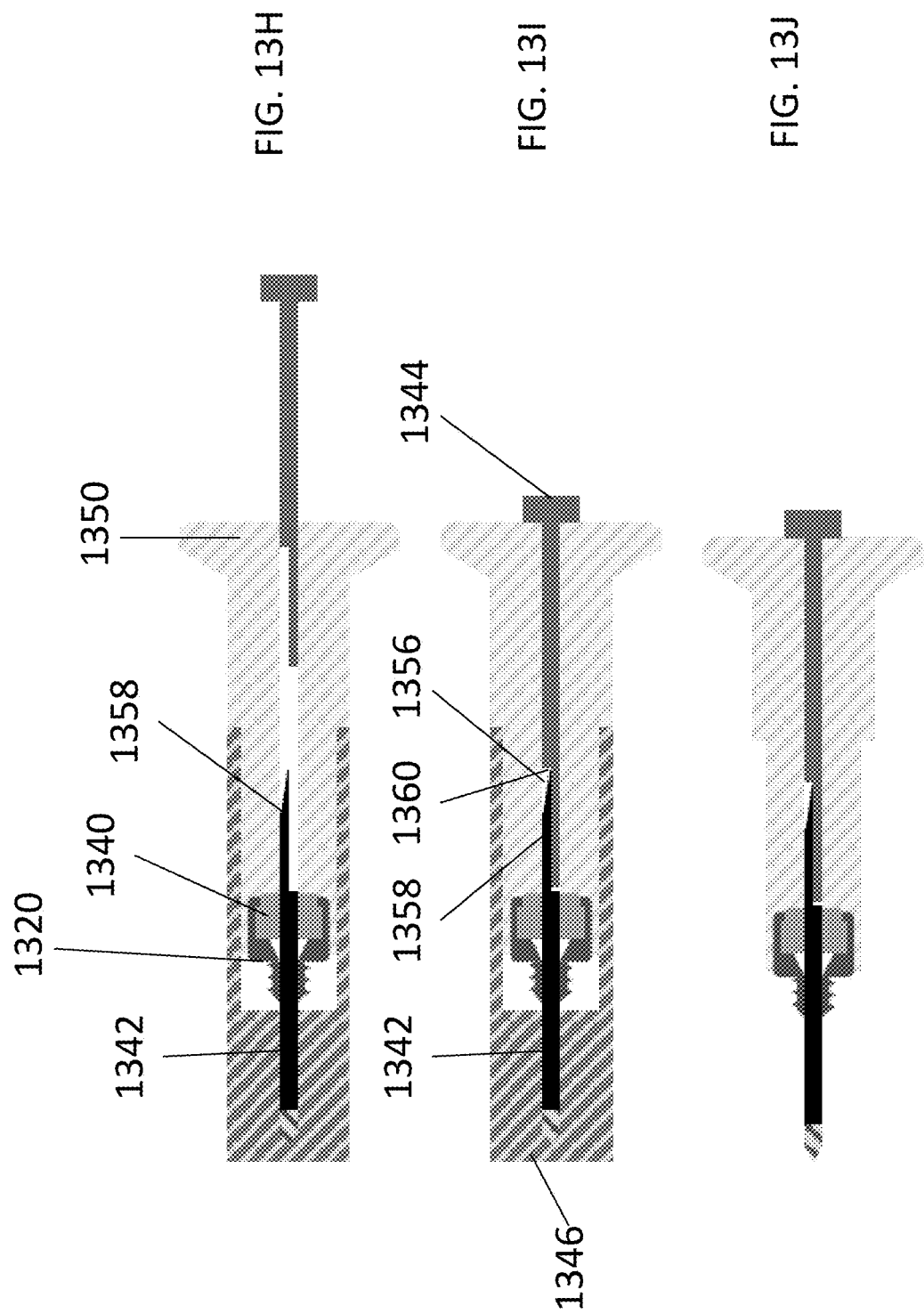

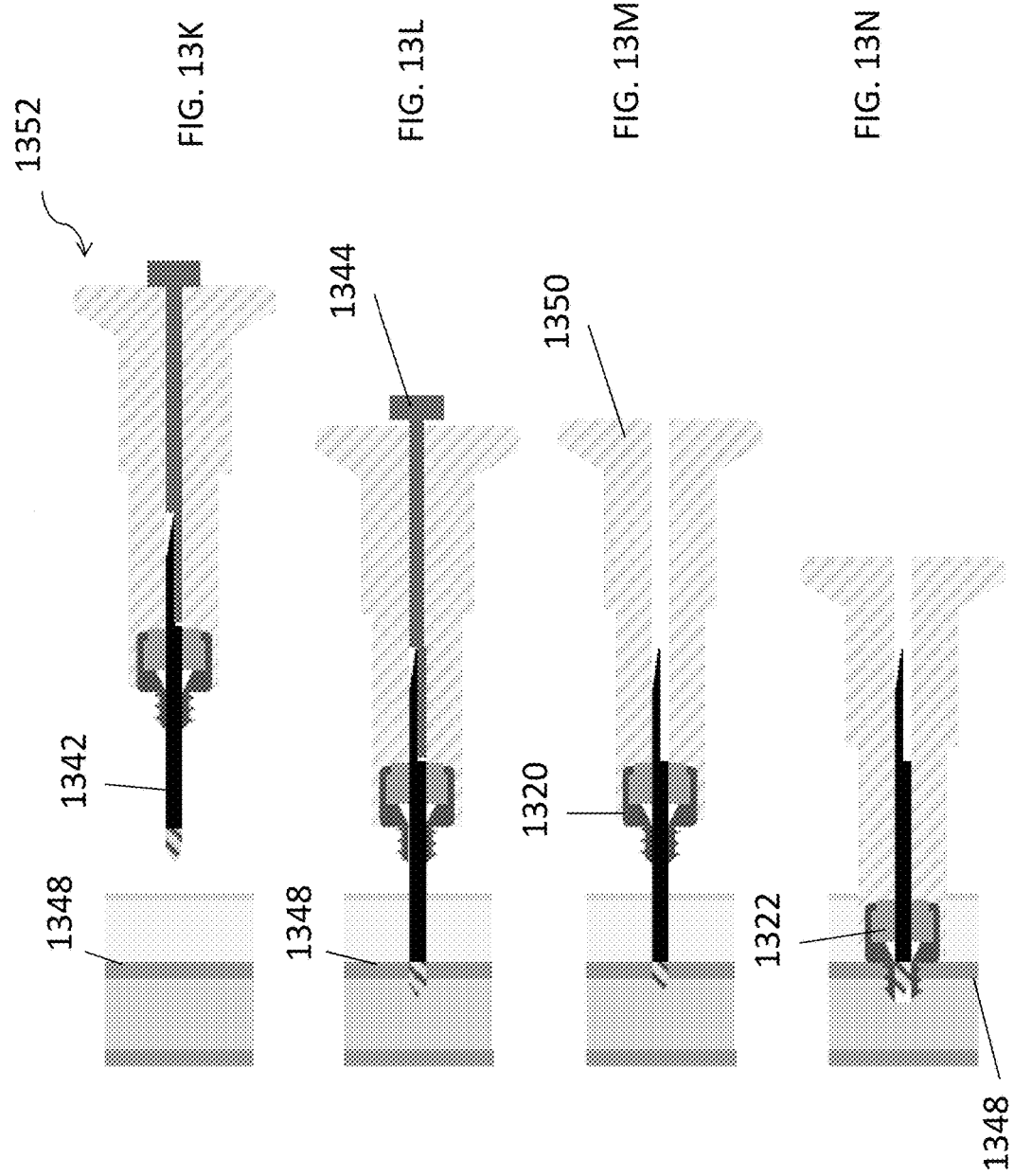

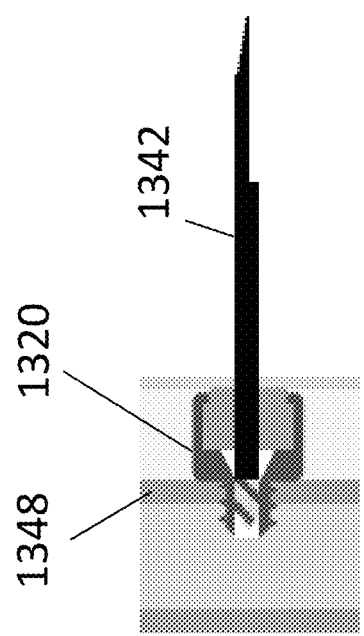
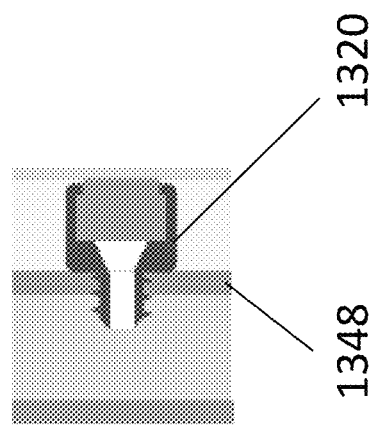
FIG. 13O
FIG. 13P

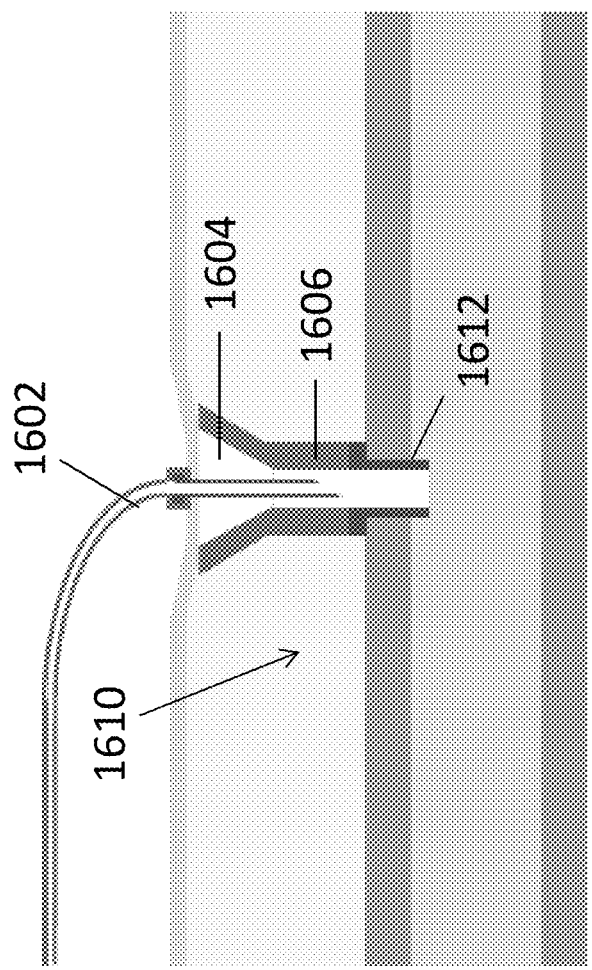

INTRAOSSEOUS INFUSION PORTS AND METHODS OF USE

CROSS-REFERENCE TO RELATED APPLICATION

This application is a divisional patent application of U.S. patent application Ser. No. 14/940,889, entitled "Intraosseous Infusion Ports and Methods of Use", filed Nov. 13, 2015, which claims priority to U.S. Provisional Patent Application No. 62/079,266, entitled "Long-term Intraosseous Infusion Ports," filed on Nov. 13, 2014, each of which are hereby incorporated by reference for all purposes in their entireties.

TECHNICAL FIELD

Example embodiments relate generally to vascular access devices (VAD). The present disclosure relates, in particular, to vascular access devices that are implantable into bone marrow cavities over a long term period for delivery of fluids.

BACKGROUND

Vascular access devices are widely used to deliver a wide variety of substances, including fluids, medications including chemotherapy, blood products and total parental nutrients. Transcutaneous vascular access devices include standard central venous catheters (CVC), tunneled central venous catheters and peripherally inserted central venous catheters (PICC). These catheters pass through the skin, enter a vein and terminate in a central venous location. They can have one or more lumens and corresponding hubs. Transcutaneous VADs can be left at the insertion site for weeks or more, and as such require regular flushes with saline or an anti-coagulant solution to protect against thrombus formation and occlusion. Other types of VADs such as totally implantable VADs are used in patients who require access for weeks to months. The implantable VADs typically have a metal or plastic port that is implanted into the subcutaneous tissue and anchored to the fascial tissue along with a catheter portion that enters a vein. The implantable VADs also require regular flushes with anti-coagulant solution, typically concentrated heparin to prevent thrombus formation and occlusion.

Currently available VADs bear significant risk (about 10%) of introducing infection to a blood stream, which can lead to serious costly complications such as bacteremia, sepsis or even death. Furthermore, because they are in constant contact with the blood stream, the VADs require regular flushes to clear stagnant blood and prevent thrombus formation and occlusion. Even with regular flushes occlusions occur in approximately 30% of patients, requiring treatment with thrombolytic agents or device removal and reinsertion of a new device, which are costly, can interfere with patient care and result in complications. In addition, most VADs require radiologic (chest radiograph or fluoroscopy) confirmation of proper positioning in a central venous location and must be carefully handled by trained clinicians. A trained clinician is required because the introduction of an even modest amount of air into the device can lead to catastrophic air embolism, which can be fatal. Still furthermore, VADs must generally terminate in, or at least in the vicinity of, the right atrium. Repeated instrumentation in chronically ill patients, such as hemodialysis patients, can lead to venous fibrosis, stenosis and occlusion, which can lead to significant morbidity and can be a formidable challenge in patients who still require vascular access.

Accordingly, there is a need for vascular access devices that are easy to implant and access, for delivering medicine and fluids to patients, which are less prone to occlusion and the various limitations outlined above.

SUMMARY OF THE INVENTION

Devices, systems and methods for vascular access devices are disclosed herein. According to embodiments illustrated herein, there is provided an infusion system that may include a chamber, where the chamber can have an inlet for receiving an insertion device. The infusion system may also include an anchor portion extending distally from the chamber and configured for secured placement in a bone. In addition, the infusion system can further include an open-ended channel extending through the anchor portion, where the channel may be in fluid communication with the chamber and can provide a substantially straight pathway that terminates at an opening at its distal end through which the insertion device can be directed towards the bone marrow.

The various embodiments illustrated herein also provided an infusion system including a first port having a chamber from which blood can be withdrawn. The system may also include a second port having a cavity in fluid communication with the chamber from the first port, where the second port may be designed to receive an insertion device. The system can further include an anchor portion extending distally from the second port for secured placement into a bone, where the anchor portion may have a channel extending from the cavity through the anchor portion and terminating in an opening so as to provide a substantially straight pathway from the cavity and through which an insertion device can be directed towards the bone marrow.

Further provided is an infusion system including an infusion device, where the infusion device may include a chamber and an anchor portion. In some embodiments, the chamber may have a proximal inlet for receiving an insertion device, and the anchor portion may extend distally from the chamber and be configured for secure the infusion device in a bone. In some embodiments, the infusion system may also include a driver mechanism for implanting the infusion device into a bone, a septum covering the proximal inlet of the chamber to prevent a reflux of infused fluids, and an open-ended channel extending through the anchor portion, where the channel may be in fluid communication with the chamber and may provide a substantially straight pathway that can terminate at an opening at its distal end through which the insertion device can exit and be directed towards the bone marrow.

Also provided is a method for operating an infusion device. In some embodiments, the method may include introducing an infusion device to a bone site. The device can have a chamber and an anchor portion, where the chamber may have a proximal inlet for receiving an insertion device. The method may further include advancing the anchor portion through a bone and into bone marrow, where the anchor portion may have an open-ended channel extending through the anchor portion. In some embodiments, the channel may be in fluid communication with the chamber, such that, when the infusion device is implanted into a bone, the channel and the chamber may create a substantially straight pathway terminating at an opening at its distal end for inserting the insertion device toward the bone marrow. In some embodiments, the method may further include inserting the insertion device through the pathway and toward the bone marrow.

BRIEF DESCRIPTION OF THE DRAWINGS

Illustrative, non-limiting example embodiments will be more clearly understood from the following detailed description taken in conjunction with the accompanying drawings.

FIGS. 1A-1J illustrate IOP devices according to various embodiments of the present disclosure.

FIGS. 4A-4C illustrate IOP devices with different length distal instraosseous portions according to various embodiments of the present disclosure.

FIGS. 8A-8C illustrate IOP devices with different geometrical configurations according to various embodiments of the present disclosure.

FIGS. 13A-13E illustrate an implantation of an IOP device using a guide wire according to various embodiments of the present disclosure.

FIGS. 13F-13P illustrate an implantation of an IOP device using an implantation kit according to various embodiments of the present disclosure.

FIG. 16A and FIG. 16B illustrate different needle guiding mechanisms for IOP devices according to various embodiments of the present disclosure.

DETAILED DESCRIPTION OF THE EMBODIMENTS

Figure 1B:
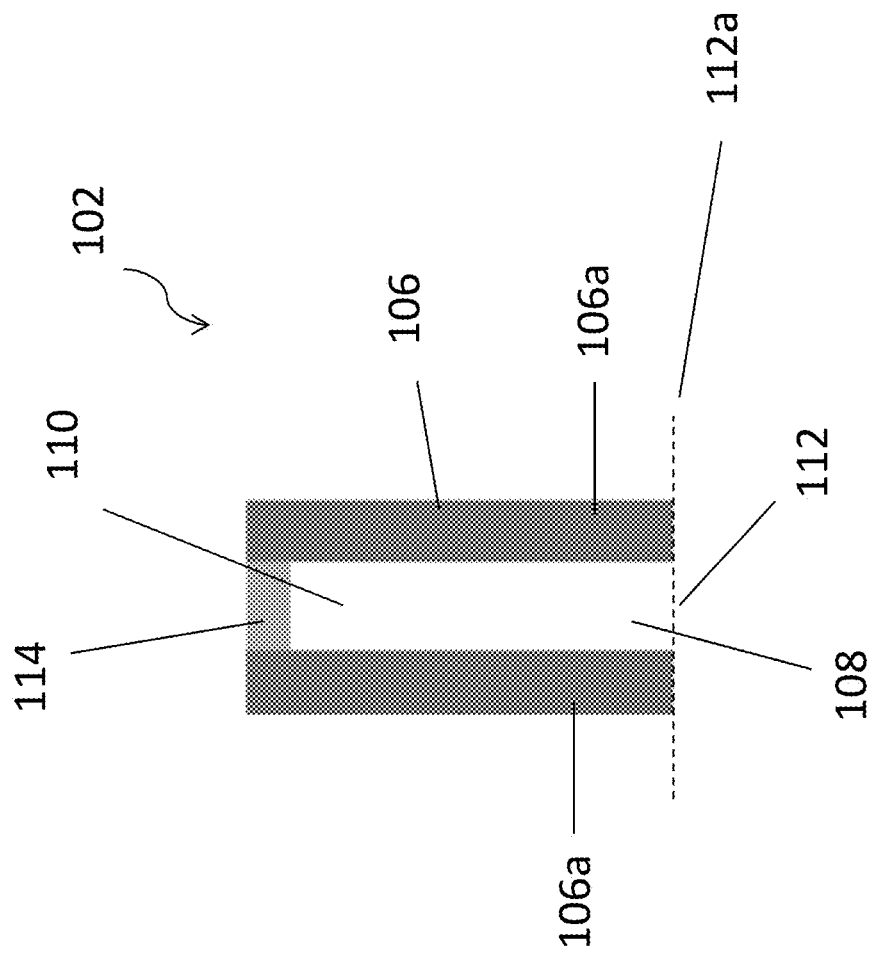

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present disclosure generally provide implantable intraosseous infusion port (IOP) devices and method of use to deliver fluids and medicines to bone marrows. The various embodiments of the present disclosure can be used to provide short or long term access to bone marrow cavities.

Figure 1C:
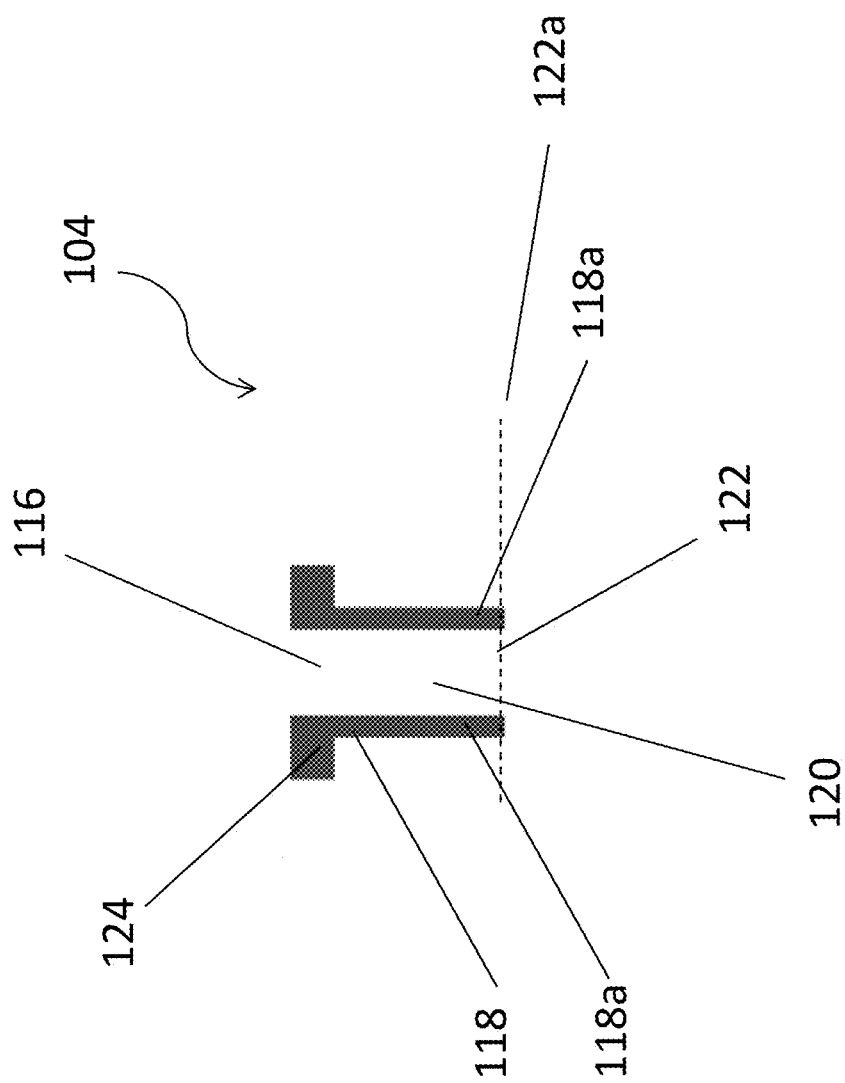
Figure 1D:
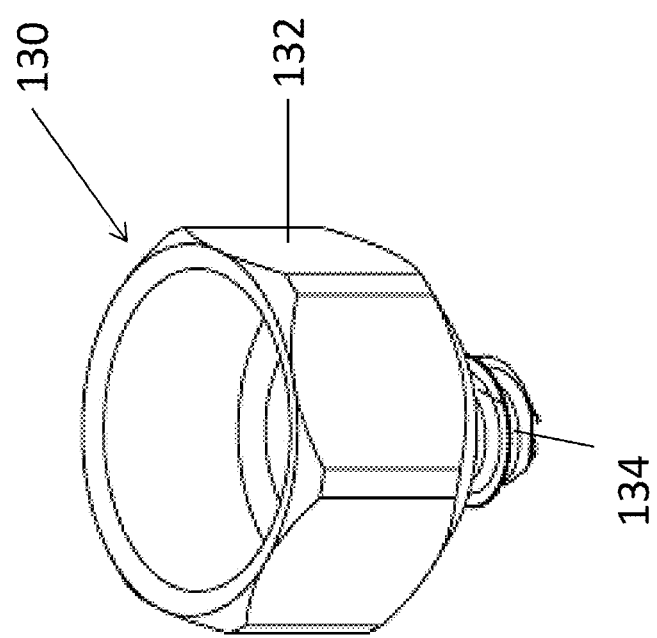

FIGS. 1A-1C illustrate an IOP device 100 in accordance with various embodiments of the present disclosure. Referring to FIG. 1A, the IOP device 100 can include a proximal subcutaneous portion 102 that may reside in soft tissues and is accessible through the skin, and a distal intraosseous or anchor portion 104 that passes through and is anchored to the cortex of a bone with its distal end residing within, or at least flush with, the marrow cavity. As illustrated in FIG. 1B, the proximal subcutaneous portion 102 can include a body portion 106 and a hollow chamber 108 with a proximal inlet 110 and a distal outlet 112. The hollow chamber 108 can be an open ended chamber where the inlet 110 and outlet 112 are oriented in a same direction as the hollow chamber 108. In some embodiments, the body portion 106 can effectively form walls 106a around the hollow chamber 108 in a vertical direction. In this fashion, the hollow chamber 108 may be a substantially straight channel housed within the walls 106a, where the outlet 112 can be an opening between the walls 106a on a plane 112a that is flush with the distal tips of the walls 106a. It should be appreciated that the body portion 106 can have any geometric shapes so long as the shape can facilitate an easy insertion of an insertion device. In some embodiments, the body portion 106 can be constructed from rigid or semi-rigid materials, such as metal, plastic or any other such biocompatible material. The proximal inlet 110 may provide access to the hollow chamber 108 and can be accessed through the skin after the implantation of the IOP device 100. All or a portion of the inlet 110 may be covered with a septum 114, through which a needle may pass to access the hollow chamber 108, to prevent reflux of the infused fluid into the subcutaneous tissue. The hollow chamber 108 may also be of any shape or size so long as fluids and medicines can be delivered through the proximal subcutaneous portion 102. In some embodiments, the hollow chamber 108 may be a channel passing through the body portion 106 of the IOP device 100, or the hollow chamber 108 may be in the form of a fluid reservoir similar to that of a traditional implantable vascular access port. When the IOP device 100 is fully assembled and implanted, the distal outlet 112 of the hollow chamber 108 will be in fluid communication with a proximal inlet 116 of the distal intraosseous portion 104 of the device 100.

Referring to FIG. 1C, the distal intraosseous portion 104 of the device 100, in some embodiments, may include a body section 118 and a channel 120 with a proximal inlet 116 and a distal outlet 122, where the distal outlet 122 may reside at a distal end of the body section 118, oriented along a same direction as the channel 120. The distal intraosseous portion 104 effectively functions as the anchor portion for the IOP device 100, anchoring the device 100 into a bone to provide access to a bone marrow cavity. In some embodiments, while the channel 120 travels in a vertical direction, the body section 118 may function as walls 118a and surrounds the channel 120. The channel 120 can be an open-ended channel terminating at the distal outlet 122. Open-ended refers to the channel 120 having, or terminates at, openings at the two ends of the channel, as illustrated in FIG. 1C. Furthermore, the distal outlet 122 can be an opening on a plane 122a that lies flush with the distal ends of the walls 118a, where the outlet 122 may be oriented in the same direction as the channel 120. In addition, the proximal inlet 116 of channel 120 may be coupled to the distal outlet 112 of the hollow chamber 108, where the channel 120 and the hollow chamber 108 effectively create a substantially straight pathway where an insertion device (e.g., needle) can travel through the pathway to reach the bone marrow cavity. In some embodiments, the distal intraosseous portion 104 may possess a proximal retaining lip 124 or other similar features for limiting the distal intraosseous portion's 104 depth of penetration into the bone marrow. The distal intraosseous portion 104 may be constructed of any rigid material that can pass through and be anchored to the bone, and it can be of any length that is capable of traversing the cortical bone. In some embodiments, the proximal subcutaneous portion 102 and the distal intraosseous portion 104 can be discrete components and implanted into a bone separately. In some embodiments, the proximal subcutaneous portion 102 and the distal intraosseous portion 104 may be discrete components connected together using means commonly practiced in the art (i.e., glue) and implanted together into a bone. In some embodiments, the proximal subcutaneous portion 102 and the distal intraosseous portion 104 may be parts to a single structure and may be implanted as a single device into a bone.

Referring to FIGS. 1D-1I, an IOP device 130 may include a proximal subcutaneous portion 132 with a hexagonal shaped body and a distal intraosseous portion 134 with threads. The hexagonal shaped body can include a plurality of surfaces for which a rotating force can be conveniently applied to drive the device 130 into a bone. The distal portion 134 may be directly connected to the proximal portion 132, where the distal portion 134 can have threads for anchoring the device 130 into the bone. In some embodiments, the diameter of the proximal portion 132 can be larger than the diameter of the distal portion 134, such that when the distal portion 134 is driven into a bone, the proximal portion 132 can function as a stopper for limiting the penetration depth of the distal portion 134. Although illustrated as hexagonal, it should be appreciated that proximal portion 132 can be provided with any geometric shape.

Figure 1E:
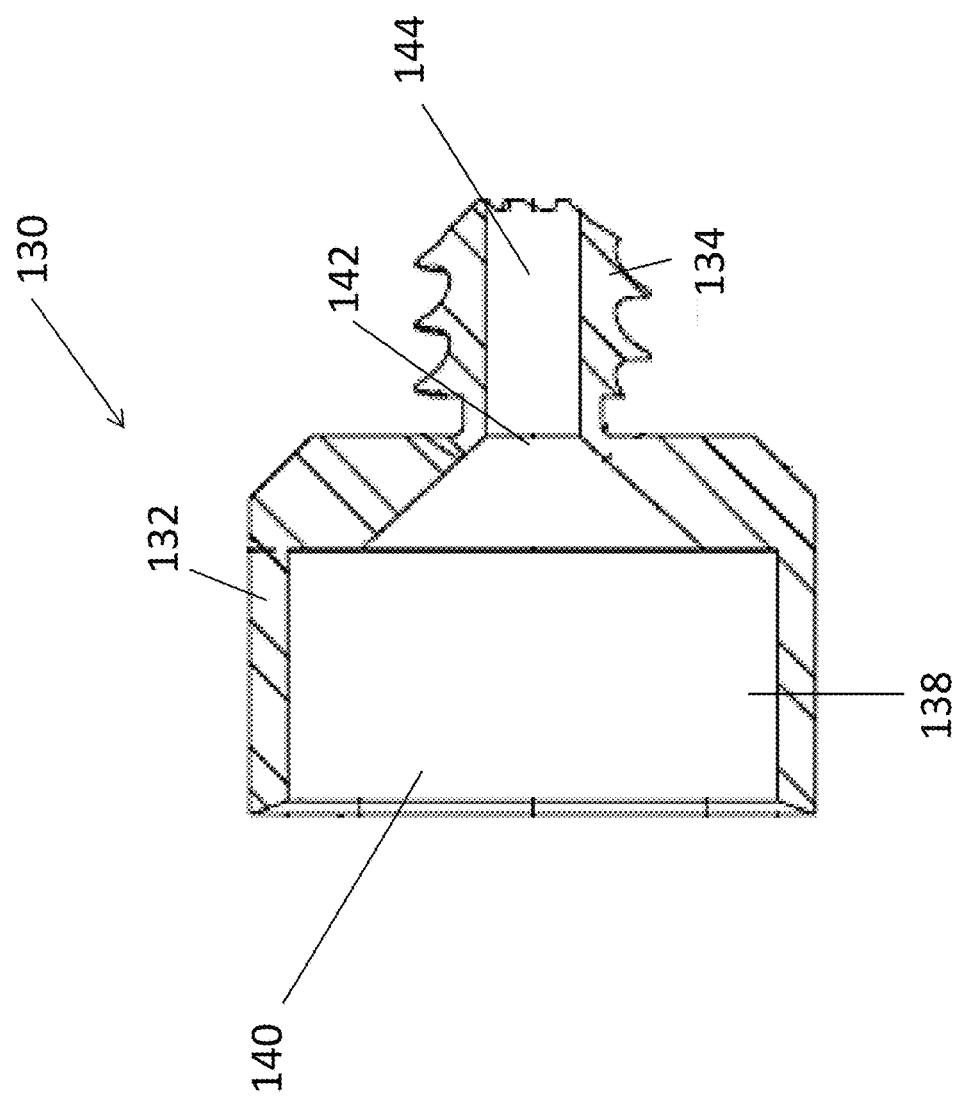

Referring now to FIG. 1E, there is shown a cross-sectional view of the IOP device 130 in detail. As illustrated in FIG. 1E, the proximal portion 132 can include a hollow chamber 138 extending through the length of the proximal portion 132. The hollow chamber 138 can function as a reservoir for holding substances that may prevent the IOP device 130 from clogging up. In some embodiments, the hollow chamber 138 may include a cubical shaped cavity 154 stacked onto a funnel shaped cavity 156. Furthermore, an inlet 140 and an outlet 141 of the hollow chamber 138 may be covered by a septum (not shown) to seal off the chamber 138. As a non-limiting example, the proximal portion 132 may have a diameter range from about 8 mm to about 20 mm and the distal portion may have a diameter range from about 5 mm to about 15 mm. The heights of the proximal portion 132 and the distal portion 134 may vary depending on the specific application the IOP device will be used for. The cubical shaped cavity 154 may have a diameter range from about 5 mm to about 15 mm and a height range from about 2 mm to about 10 mm. The funnel shaped cavity 156 may have an upper diameter range from about 5 mm to about 15 mm, a lower diameter range from about 3 mm to about 8 mm and a slope range from about 30 to about 60 degrees. In some embodiments, when anchored to a bone, the hollow chamber 138 may be sealed off at the inlet 140 with materials that may be penetrated by a needle, thereby effective sealing off the IOP device preventing a reflux of the infused fluid into the subcutaneous tissue.

Still referring to FIG. 1E, the distal portion 134 may include a channel 144 extending through the length of the distal portion 134. In some embodiments, the channel 134 may range from about 1 mm to about 5 mm in diameter, wide enough for passing through a needle designed for medical applications. The channel 144 may be in fluid communication with the hollow chamber 138 and be configured to allow an insertion needle or catheter to extend towards the bone marrow cavity, when the IOP device 130 is implanted into a bone.

Figure 1F:
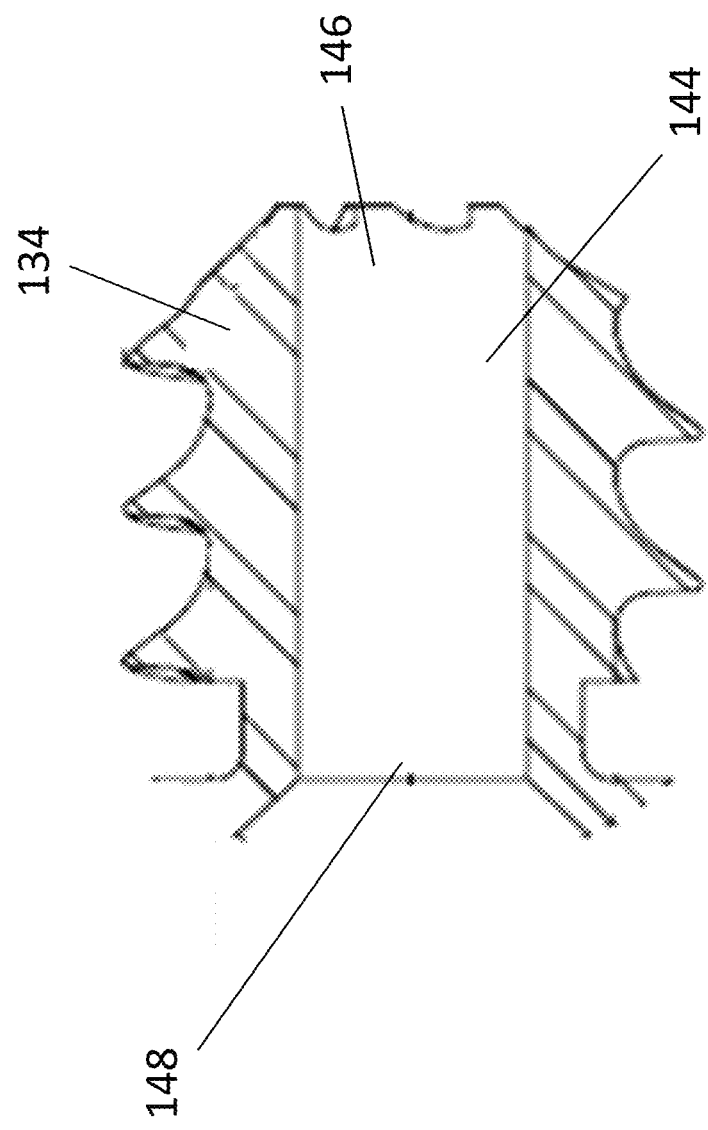

Refer now to FIG. 1F, FIG. 1F shows a cross sectional view of the distal portion 134 where the channel 144 may include an inlet 148 located at the proximal end of the distal portion 134. In some embodiments, the inlet 148 may be directly connected to the outlet 142 of the hollow chamber 138. The channel 144 may further include an outlet 146 located at a distal most tip of the distal portion 134, such that when the IOP device 130 is implanted in a bone, the outlet 146 may provide an access opening to the bone marrow cavity at a distal most penetration depth achievable by the IOP device 130. Furthermore, the inlet 148 and the outlet 146 of the channel 144 may be aligned along a straight path such that a straight needle entering through the inlet 148 can travel through the channel 144 and exit at the outlet 146 to reach the bone marrow cavity.

Referring now to FIGS. 1G-1J, illustrated are diagrams of the IOP device 130 in three-dimensional views. In some embodiments, the IOP device 130 may include a sealing member such as a septum 150, where the septum 150 may be penetrated by an insertion device when the IOP device 130 is in use. In some embodiments, the septum 150 may be a rubber septum or any material that can be penetrated while maintaining a seal. The septum 150 may be designed to have a diameter large enough to seal off the inlet 140 such that a reflux of the infused fluid into the subcutaneous tissue may be prevented. As illustrated in FIG. 1G, the septum 150 may be secured inside the hollow chamber 138 by a stopper member 152, where the stopper member may have the shape of a ring. FIG. 1H provides a cross sectional view of the IOP device 130 where the septum 150 is securely placed inside the hollow chamber 138 by the stopper member 152. FIG. 1I is another diagraming illustrating the IOP device 130 with the septum 150 inserted into the hollow chamber 138, where the septum 150 may be penetrated by an insertion device such as a needle to reach a bone marrow cavity. In some embodiments, as illustrated in FIG. 1J, an IOP device 160 may further include a guide path 162 for removing grinded bones during self-drilling operations.

Figure 2:
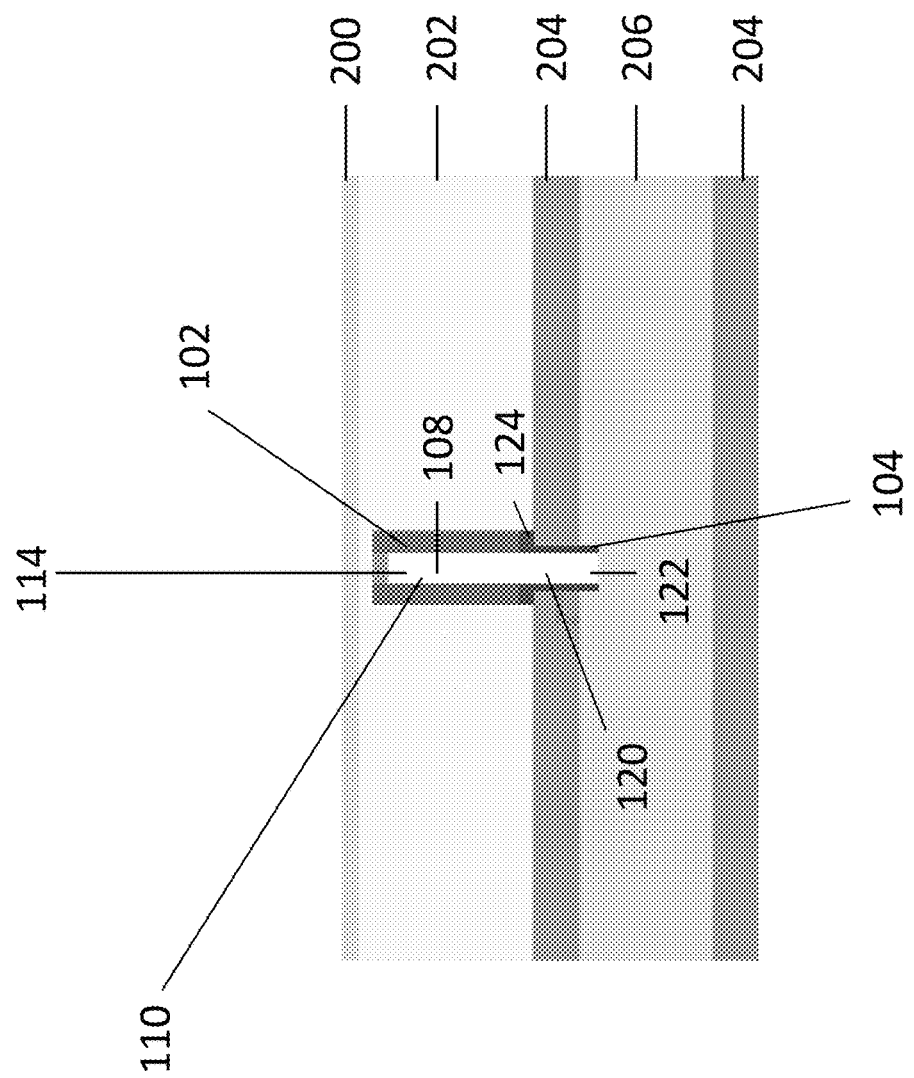
FIG. 2 illustrates an IOP device implanted into a bone according to various embodiments of the present disclosure.

When fully implanted into tissue, as illustrated in FIG. 2, the proximal subcutaneous portion 102 of the IOP device 100 can be substantially submerged underneath a layer of skin 200 and within a layer of subcutaneous tissue 202. In some embodiments, the proximal portion 102 may be entirely submerged and may be coupled to the distal intraosseous portion 104 at the retaining lip 124 where the hollow chamber 108 can be in fluid communication with the channel 120. The distal intraosseous portion 104 may be anchored through a cortex layer 204 and into the bone marrow 206, such that the distal outlet 122 may be in direct contact with the bone marrow 206. A needle may be used to penetrate through the septum 114 covering the proximal inlet 110 and deliver fluids to the bone marrow through the channel 120.

It should be appreciated that IOP devices illustrated in the various embodiments presented herein do not necessarily possess an intravascular component and does not come into contact with the blood stream, as such, the risk of blood-borne infections and their sequelae can be expected to be significantly lower compared to conventional VADs. Secondly, because the IOP device 100 communicates directly with the bone marrow cavity as opposed to a vascular structure with free-flowing blood, the need for regular flushes and the risk of thrombosis and occlusion should likewise be minimal. As a result, the device 100 does not require a fluid reservoir although one may be provided for other purposes. Similarly, unlike conventional VADs, the IOP device 100 presented herein does not dependent on maintaining a clear fluid filled channel through the device. The device 100 can be utilized even if the channel is clogged by clots or other debris by using a long access needle which extends through the device directly into the marrow. In some embodiments, the IOP device 100 can operate without a fluid channel but just a pathway for the access needle to come in contact with the bone marrow. In addition, IOP devices presented by the present disclosure also have a superior safety profile since the accidental introduction of air into the marrow cavity does not carry the same risk as into the bloodstream.

Furthermore, unlike conventional VADs, where the VADs can be utilized in limited anatomic structures, the IOP device of the present disclosure can be inserted into any bone with a marrow cavity, even at multiple sites within the same bone, potentially providing an unlimited number of operable sites. In addition, IOP devices of the present disclosure will generally not require radiologic confirmation of position, unlike conventional VADs. Although the IOP devices of the present disclosure may require surgical implantation, they lack of a bulky reservoir which allows for a more streamlined device that can be inserted in a near-percutaneous fashion. Still furthermore, biodegradable components may be used to construct the IOP devices which can eliminate the need for surgical removal.

Figure 3C:
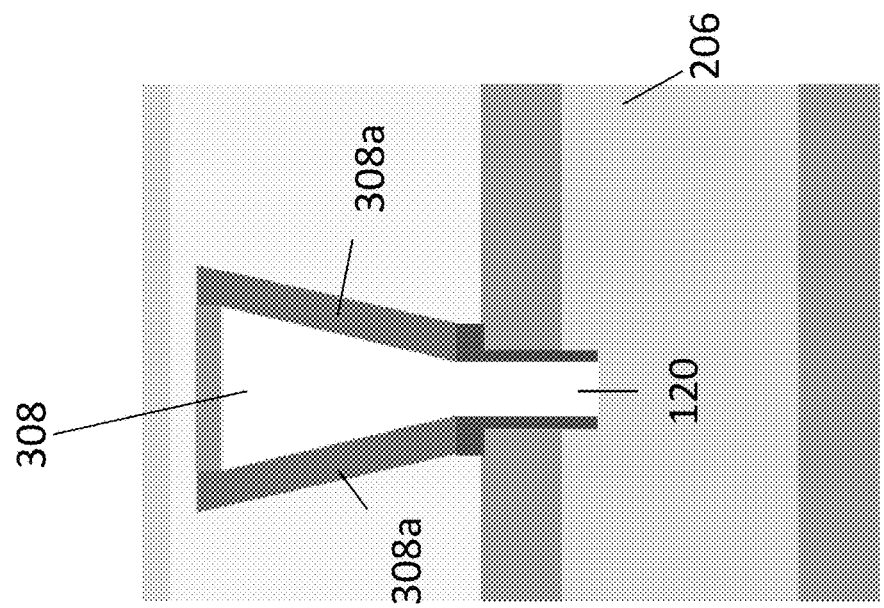
FIGS. 3A-3C illustrate IOP devices with differently shaped hollow chambers according to various embodiments of the present disclosure.
Figure 3B:
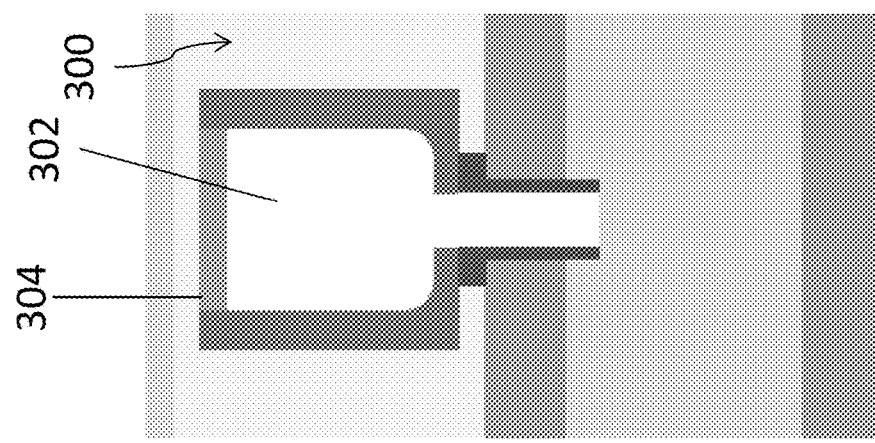
Figure 3A:
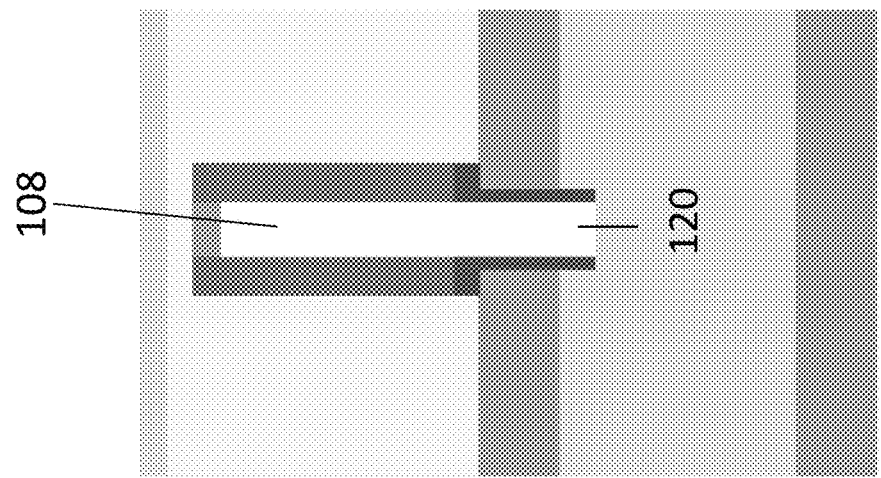

In some embodiments, the hollow chamber 108 can assume various geometric configurations to facilitate the delivery of fluids and medicines through the channel 120. Referring to FIG. 3A, where a straight through hollow chamber 108 may be utilized to provide direct fluid communication with channel 120. Fluids and medicines can be directly delivered through the hollow chamber 108 and channel 120 to the bone marrow cavity 206. In some embodiments, a hollow chamber 108 may assume the shape and function of a fluid reservoir 302 similar to that of a transitional implantable vascular access ports. As illustrated in FIG. 3B, the fluid reservoir 302 may be sealed from by a septum 304 similar to that of the hollow chamber 108. This configuration as shown in FIG. 3B advantageously allows longer intervals between catheter flushes, which significantly reduces the complexities involved in patient cares. In addition, the larger subcutaneous portion as illustrated in FIG. 3B facilitates the use of the IOP device 100 by providing the clinician with a larger, more easily palpable target underneath the skin to penetrate with the needle. In some embodiments, a hollow chamber may assume a geometric shape for guiding needles and catheters for an easy insertion through the IOP device 100. Referring to FIG. 3C, a hollow chamber 308 may assume a concaved shape with sloped walls 308a, where the walls 308a of the hollow chamber 308 can guide an insertion needle to the channel 120.

In some embodiments, the distal intraosseous portion 104 can vary in length to accommodate for different cortical thicknesses and bone marrow cavity diameters. For example, the distal intraosseous portion 104 can be short in length where the distal outlet 404 flushes with the inner cortical surface 402a of a cortical bone 402, as illustrated in FIG. 4A, or it can extend for a small amount into the marrow cavity 406, as illustrated in FIG. 4B, or well into the marrow cavity 406 as illustrated in FIG. 4C.

Figure 5C:
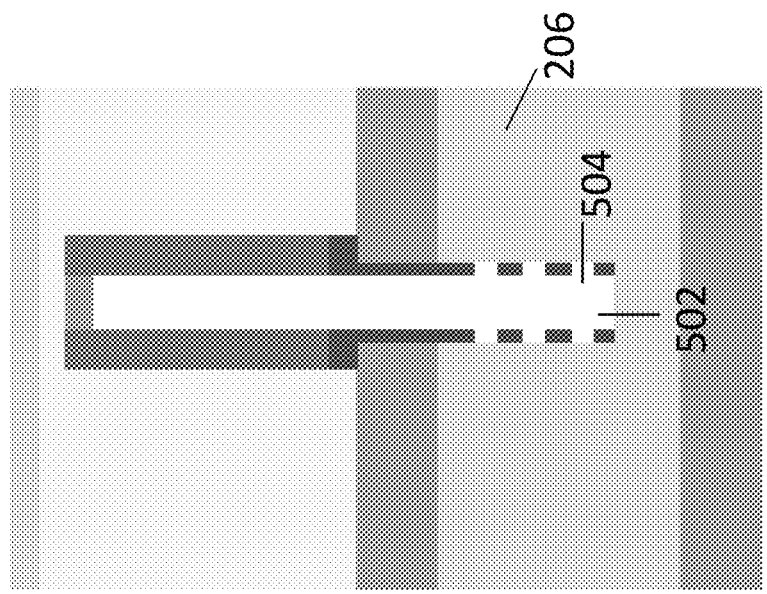
FIGS. 5A-5C illustrate distal instraosseous portions with different types of infusion holes according to various embodiments of the present disclosure.
Figure 5B:
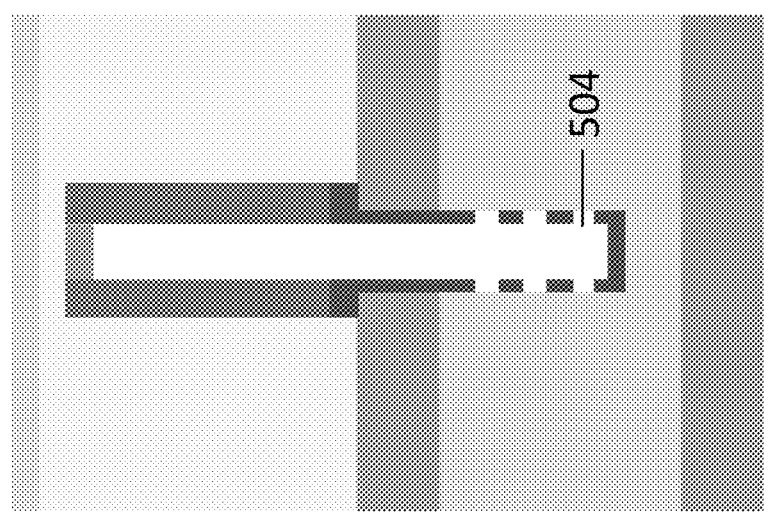
Figure 5A:
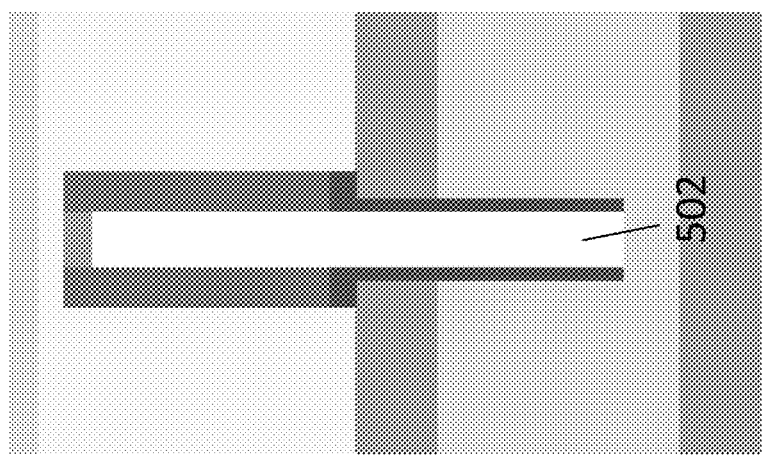

Referring now to FIGS. 5A-5C, in some embodiments, to better accommodate the delivery and distribution of fluids and medicine to and from the bone marrow 206, the distal outlet 122 of the IOP device 100 may consist of an end hole 502, as illustrated in FIG. 5A, or one or more side holes 504 with a capped off distal end to provide a stop to prevent the needle from actually entering the bone marrow, as illustrated in FIG. 5B, or a combination thereof, as illustrated in FIG. 5C to provide multiple pathways for fluid flow decreasing the resistance to flow and the propensity for clogging.

Figure 6C:
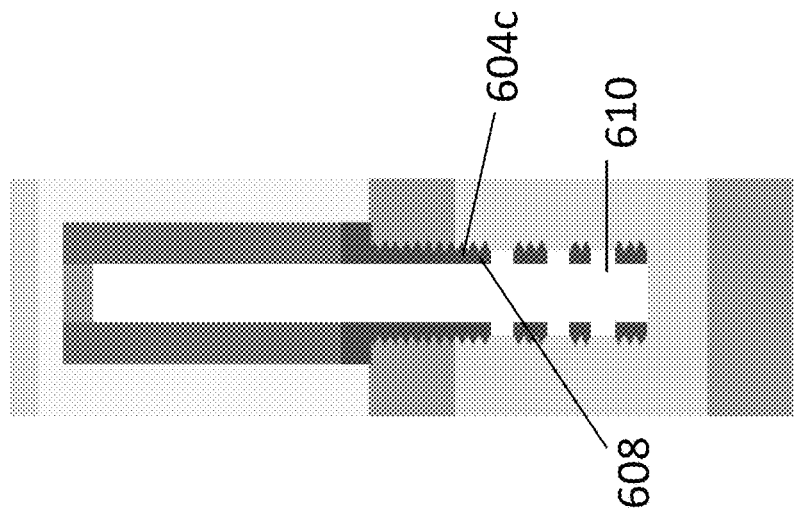
FIGS. 6A-6E illustrate distal instraosseous portions with different anchoring mechanisms according to various embodiments of the present disclosure.
Figure 6B:
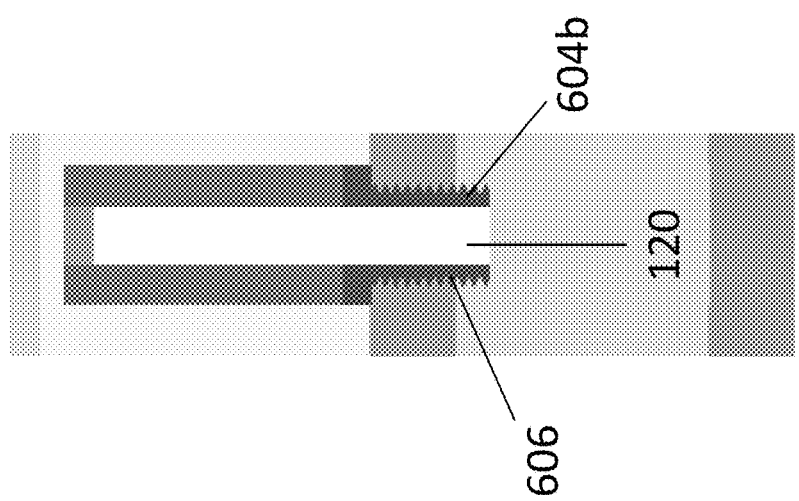
Figure 6A:
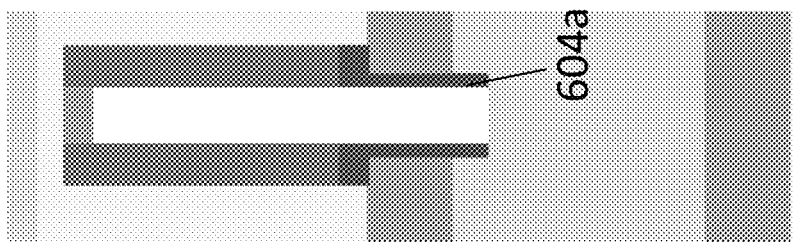
Figure 6E:
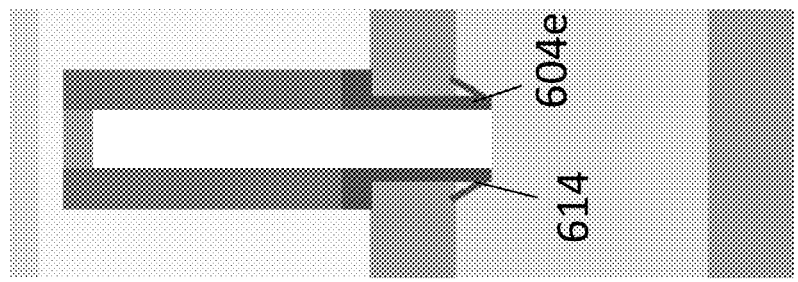
Figure 6D:
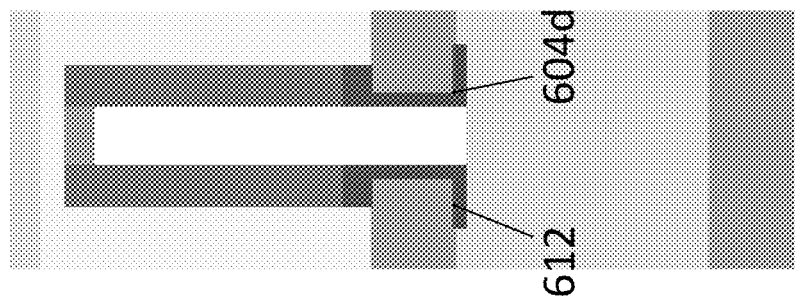

In some embodiments, when the device 100 is fully assembled and implanted, the distal intraosseous portion 104 may be anchored into a bone 602. This may be accomplished in a variety of ways as illustrated in FIGS. 6A-6E. For example, a distal intraosseous portion 604*a* may be anchored through a cortex layer 602 using friction, as shown in FIG. 6A. In some embodiments, referring to FIG. 6B, however, a distal intraosseous portion 604*b* may include an outer surface with screw like threads 606 designed to lodge into the cortex layer 602. In some embodiments, as illustrated in FIG. 6C, a threaded surface 608 may also include one or more side holes 610 through which the fluid may egress. The screw like threaded surface design can be self-tapping and self-drilling or may require pre-drilling. In some embodiments, referring to FIG. 6D, a distal intraosseous portion 604*d* may include a T-bar 612 or starfish (not shown) shaped anchoring/retaining mechanism for anchoring the distal intraosseous portion 604*d* into the cortex layer. In some embodiments, as illustrated in FIG. 6E, a distal intraosseous portion 604*e* may use a barb shaped anchoring mechanism 614 for anchoring into the cortex layer.

Figure 7D:
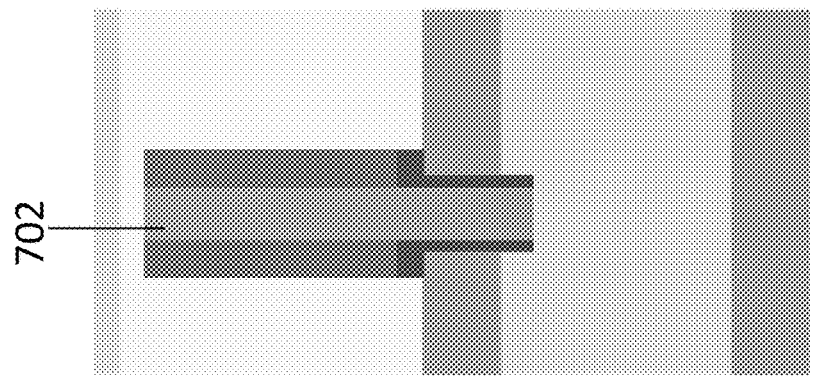
FIGS. 7A-7D illustrate the septum occupying different portions of the hollow channel according to various embodiments of the present disclosure.
Figure 7C:
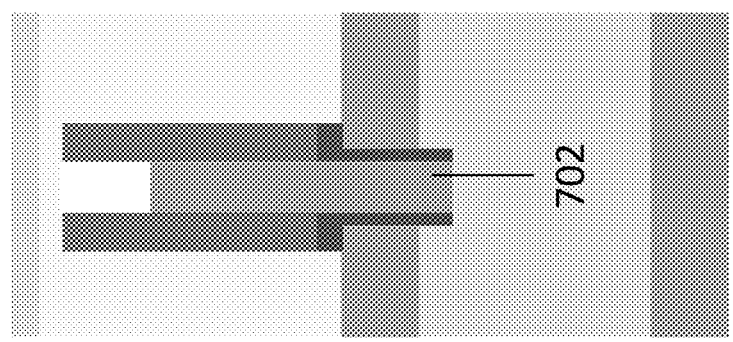
Figure 7B:
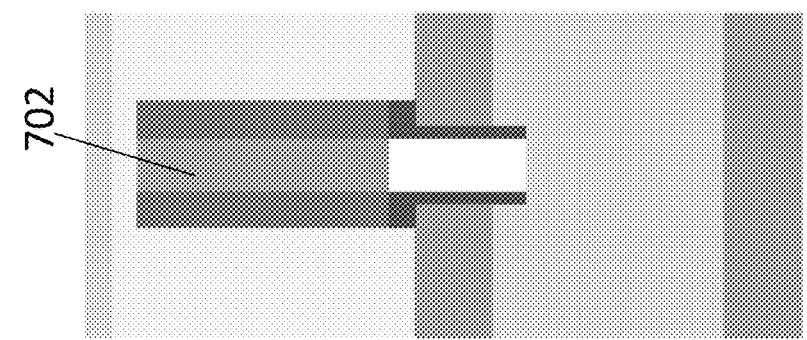
Figure 7A:
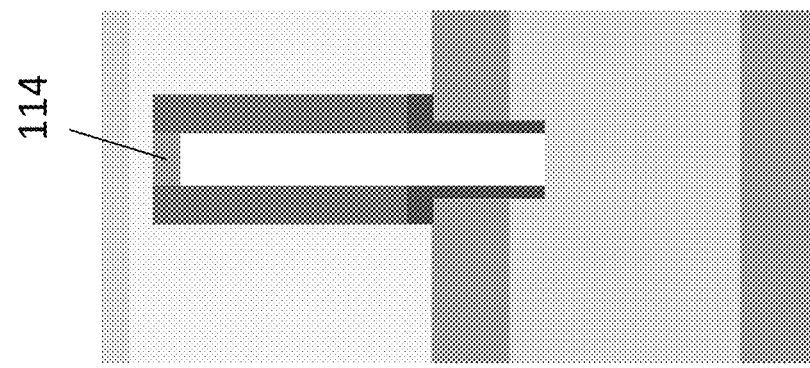

In some embodiments, the hollow chamber 108 of the proximal subcutaneous portion 102 and the channel 120 of the distal intraosseous portion 104 may be partially or complete occupied with materials that can be penetrated with the needle. For example, instead of having the septum 114 covering the proximal inlet 110 of the proximal subcutaneous portion 102 of the IOP device 100, as illustrated in FIG. 7A, the same rubber material 702 may extend towards or all the way to the distal outlet 122 of the distal intraosseous portion 104, as shown in FIGS. 7B-7D. In some embodiments, the hollow space within the device 100 may be eliminated, thereby reducing or eliminating the risk of clogging the device with debris or thrombosis, enhancing its functionality during long-term use.

In some embodiments, when fully assembled and implanted, the proximal subcutaneous 102 and distal intraosseous 104 portions of the device 100 may form a single structure. In this configuration, the distal outlet 112 of the proximal subcutaneous 102 and proximal inlet 116 of the distal intraosseous 104 can form a continuous pathway, as shown in FIG. 8A. In some embodiments, to better assist the insertion of a needle or catheter into the bone marrow, a proximal subcutaneous portion 802 and a distal intraosseous portion 804 may both be positioned orthogonal to the bone, as illustrated in FIG. 8B. In some embodiments, referring to FIG. 8C, a proximal subcutaneous portion 806 and a distal intraosseous portion 808 may be angulated to facilitate insertion needle access and optimize the ergonomics of the use of the device.

Figure 9:
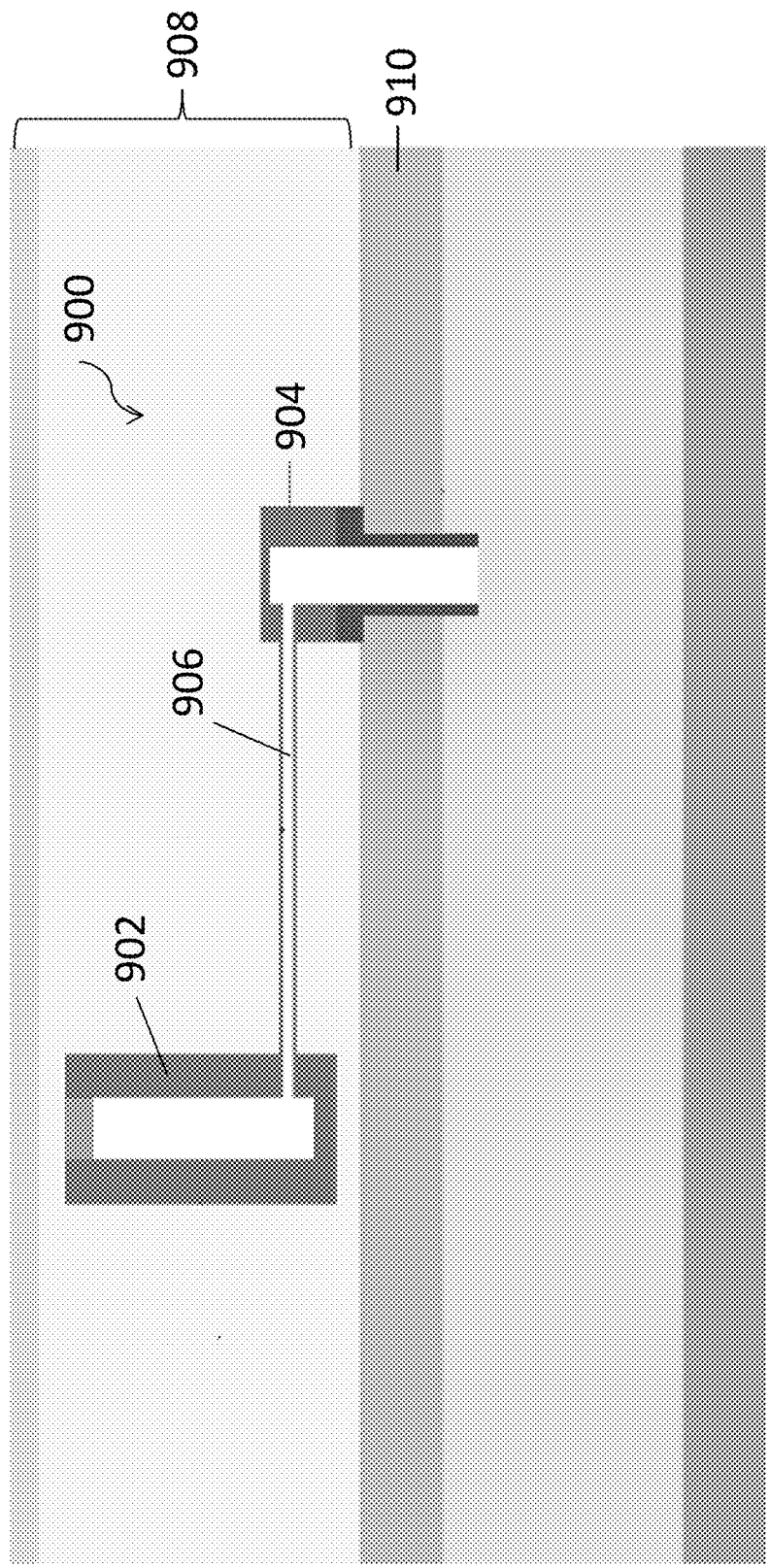
FIG. 9 illustrates a multi-bodied IOP device according to various embodiments of the present disclosure.

In some embodiments, as illustrated in FIG. 9, an IOP device 900 can include discrete proximal subcutaneous 902 and distal intraosseous portions 904 connected by a length of tubing 906 or other discrete channel which passes through the soft tissues 908 and in fluid communication with the discrete proximal 902 and distal 904 portions. This configuration allows the transcutaneous access site to be remote from the intraosseous infusion site. This enhances the functionality of the device by allowing the intraosseous infusion portion to be implanted in a bone location which may not be easily accessible on a routine basis. For example, the intraosseous portion may be implanted in the pelvic bone while the transcutaneous access site may be more conveniently located in the lower abdominal wall.

To implant the device 900, firstly a site for insertion of the distal intraosseous portion 904 into the bone may be selected, prepped, draped, and anesthetized. Then a separate second site for placement of the proximal subcutaneous portion 902 may also be selected, prepped, draped and anesthetized. Subsequently, stab incisions are made at each site. The intraosseous portion 904 may then be passed through the first site and is implanted into a bone 910. The subcutaneous portion 902 may then be inserted into the second site and anchored to the surrounding soft tissues 908.

The connecting tubing 906 may be tunneled through the soft tissue 908 between the sites and can be connected to the proximal 902 and distal 904 portions respectively. In some embodiments, the connecting tubing 906 may come pre-attached to either the proximal 902 or distal 904 portions, eliminating the need to make additional connections. In some embodiments, the proximal portion 902 may be a small hub, the entire device 900 can then be preassembled and the proximal portion 902 can be advanced along with a catheter through a soft tissue tunnel until it lies in the soft tissue under the second site, eliminating the need for the second incision. Once the device 900 has been properly implanted, the flow in the device 1310 may be tested and if adequate the stab incisions may be closed.

Figure 10A:
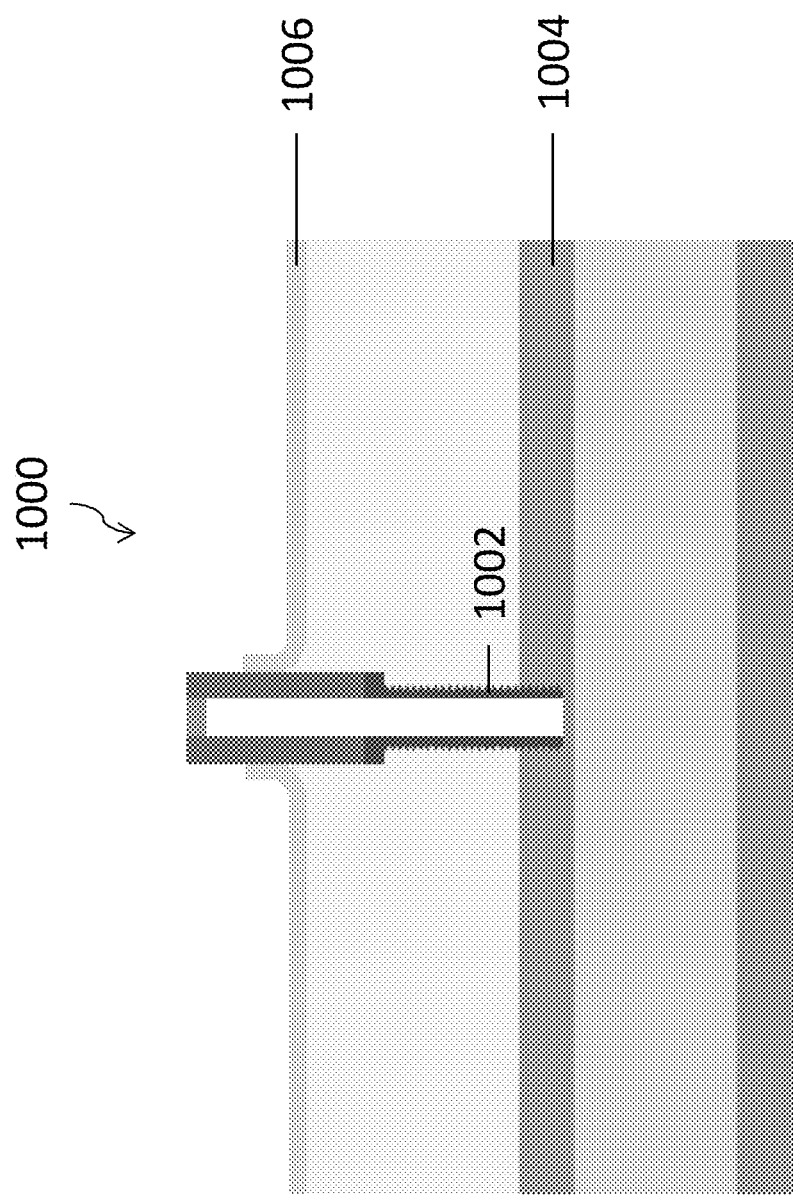
FIG. 10A and FIG. 10B illustrate an implantation of a single structured IOP device according to various embodiments of the present disclosure.
Figure 10B:
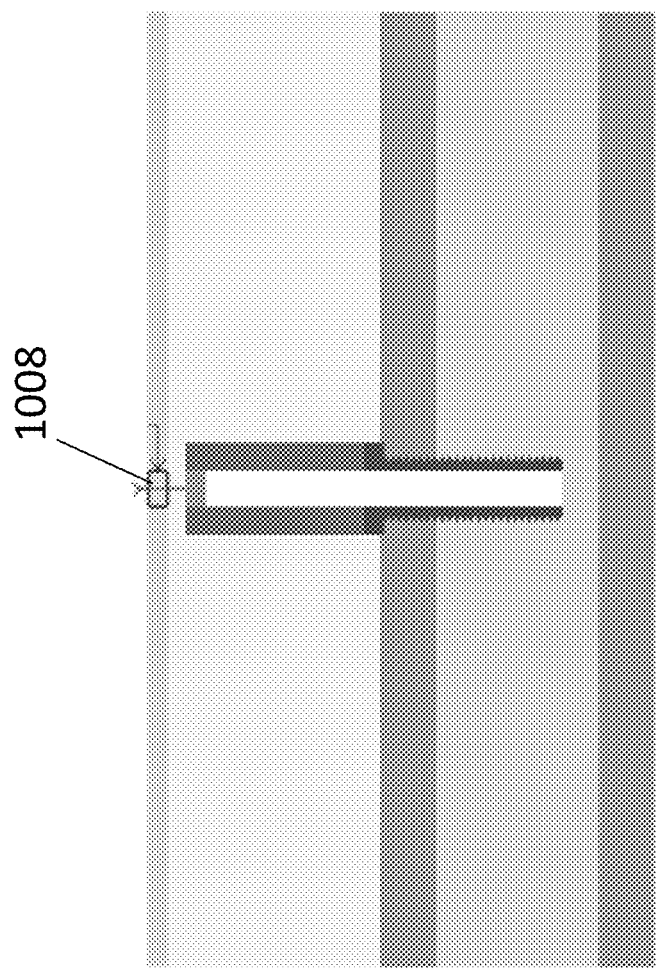

The IOP devices presented by the present disclosure may be implanted as a whole or in parts. Referring to FIG. 10A and FIG. 10B, an IOP device 1000 may be provided as a whole. The IOP device 1000 may include a screw like threaded surface 1002 for anchoring the device at the cortex layer 1004. The device 1000 can be advanced through the cortex layer 1004 in a rotating fashion. Once the device 1000 is implanted underneath a layer of skin, the incision opening can be sutured to prevent infections.

Figure 11A:
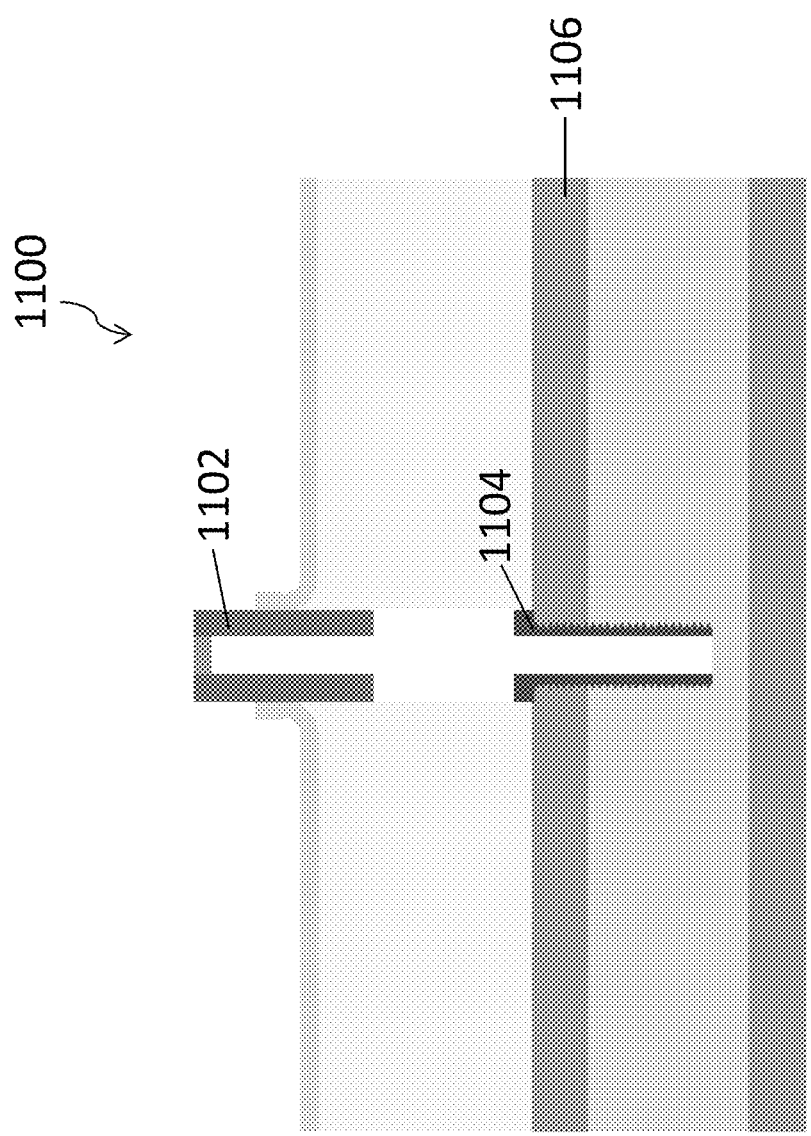
FIG. 11A and FIG. 11B illustrate an implantation of a multi-structured IOP device according to various embodiments of the present disclosure.
Figure 11B:
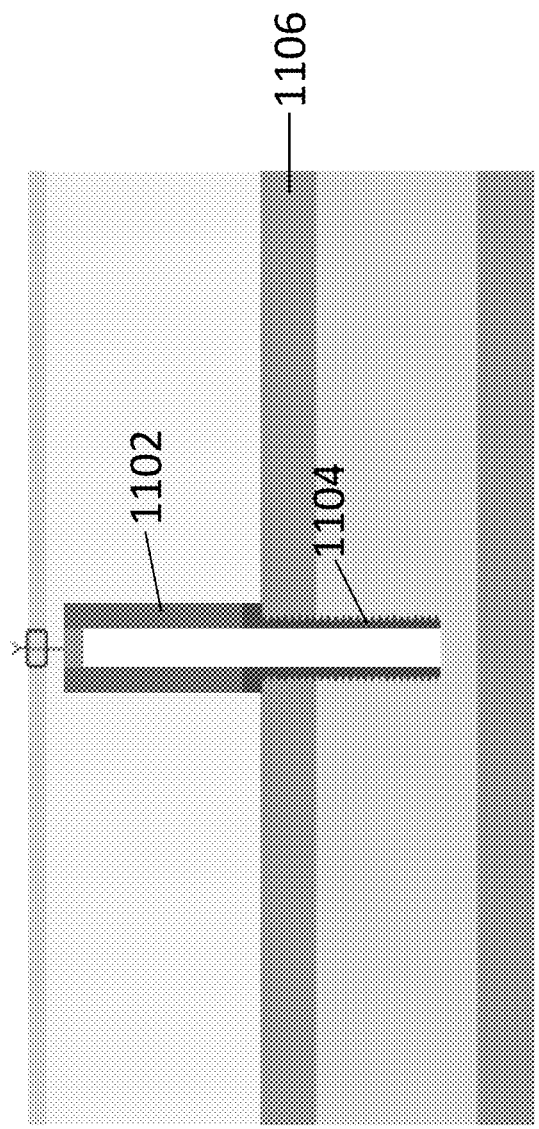

In some embodiments, referring to FIG. 11A and FIG. 11B, a distal intraosseous portion 1104 of an IOP device 1100 may be inserted first using an appropriate instrument. Once anchored into the bone 1106, the proximal subcutaneous portion 1102 can then be attached to the distal intraosseous portion 1104.

Figure 12A:
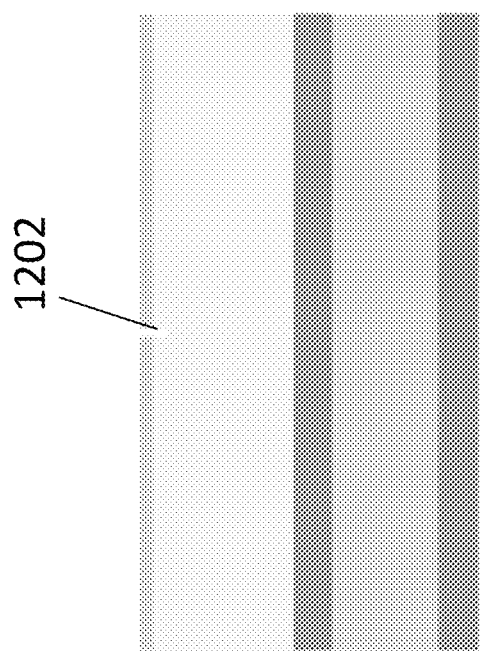
FIGS. 12A-12C illustrate an implantation of an IOP device without using guide wires according to various embodiments of the present disclosure.
Figure 12B:
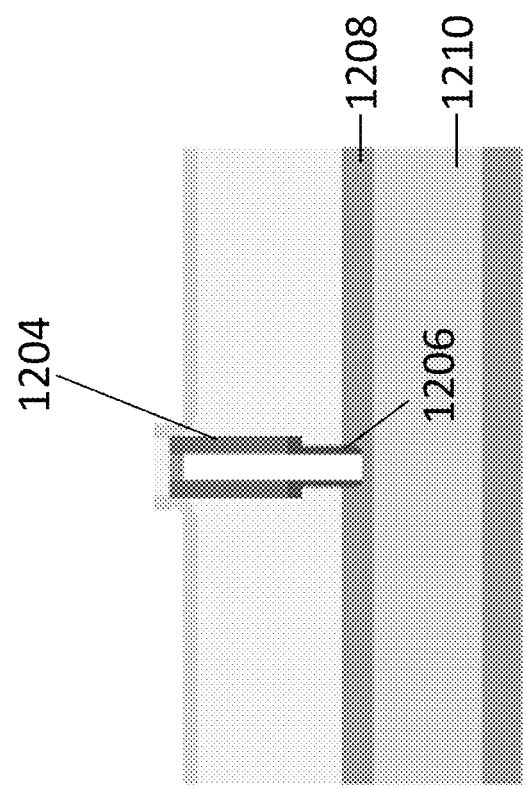
Figure 12C:
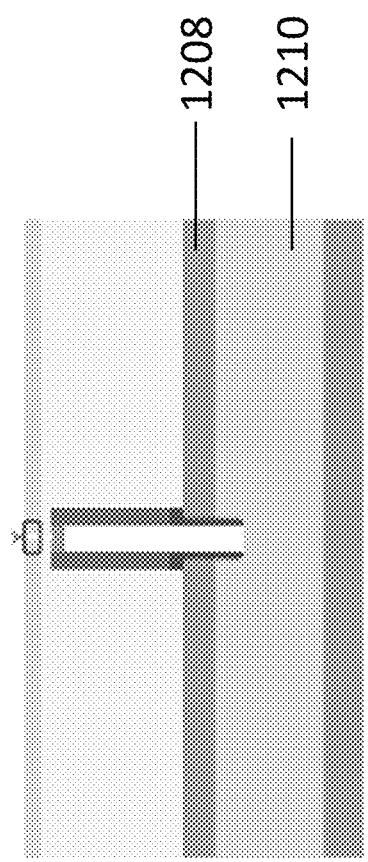

In operation, an IOP device 1204 can be implanted as a single structure as illustrated in FIGS. 12A-13E. Referring to FIG. 12A, an operator can firstly identify an implantation site. The site may be any site where the surface of a bone is relatively close to the surface of the skin. Possible sites include, but are not limited to, the clavicle, sternum, iliac crest, skull and long bones of the arm (humerus, radius, ulna) or leg (tibia, fibula). Subsequently the bone can be palpated and the skin over the bone can be prepped with appropriate antiseptics and draped in the usual sterile fashion. After appropriate local, regional or general anesthesia, a small stab incision 1202 can be made in the skin. The IOP device 1204 can then be inserted through the incision 1202, as shown in FIG. 12B, until a distal portion 1206 of the device 1202 engages a cortex layer 1208 of the bone. The device 1204 can subsequently be advanced towards a bone marrow cavity by rotating the device 1204. Once the distal portion 1206 of the device 1204 advances through the cortex layer 1208 and come into direct contact with a bone marrow cavity 1210, as shown in FIG. 12C, the distal portion 1206 can be anchored into the cortex layer 1208.

Figure 13A:
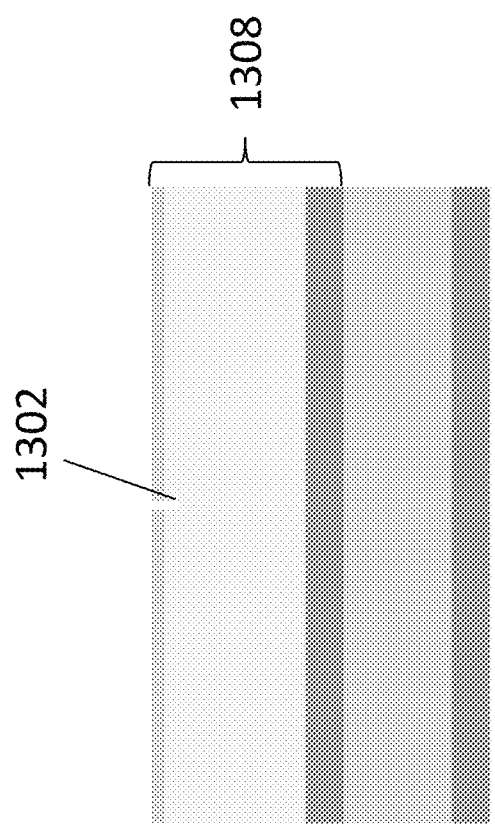

In some embodiments, as illustrated in FIGS. 13A-13E, after an incision 1302 has been made at an insertion site as shown in FIG. 13A, a guide wire 1304 may be firstly inserted through the incision 1302 and into the bone 1306, as illustrated in FIG. 13B and FIG. 13C. The guide wire 1304 may be used to guide an IOP device through soft tissue layers to the surface of a bone such that extensive surgical exposure may be avoided. In some embodiments, the guide wire 1304 may include measurement markings 1388 designed for measuring the soft tissue 1308 and/or bone 1306 thickness. For example, when inserted into a bone, an operator may read off the markings to determine the thickness of the subcutaneous tissue layer, such that an appropriate sized device can be selected based on the thickness of the soft tissue 1308 and bone 1306. In some embodiments, the guide wire may include a ledge in proximity to its distal end to serve as a stopping member to the penetrating distal end. This ledge may prevent a further penetration of the guide wire into a bone marrow such that an operator may collect thickness measurements on the subcutaneous tissue. In some embodiments, the guide wire may include an activation mechanism (i.e., spring) designed to activate a hinge at the distal end of the guide wire, such that the hinge may engage onto an inside surface of a cortex bone layer, allowing an operator to measure the thickness of the bone and the subcutaneous tissue. Before being implanted, an IOP device 1310 can be flushed with saline or other fluid to evacuate any air within it.

Figure 13D:
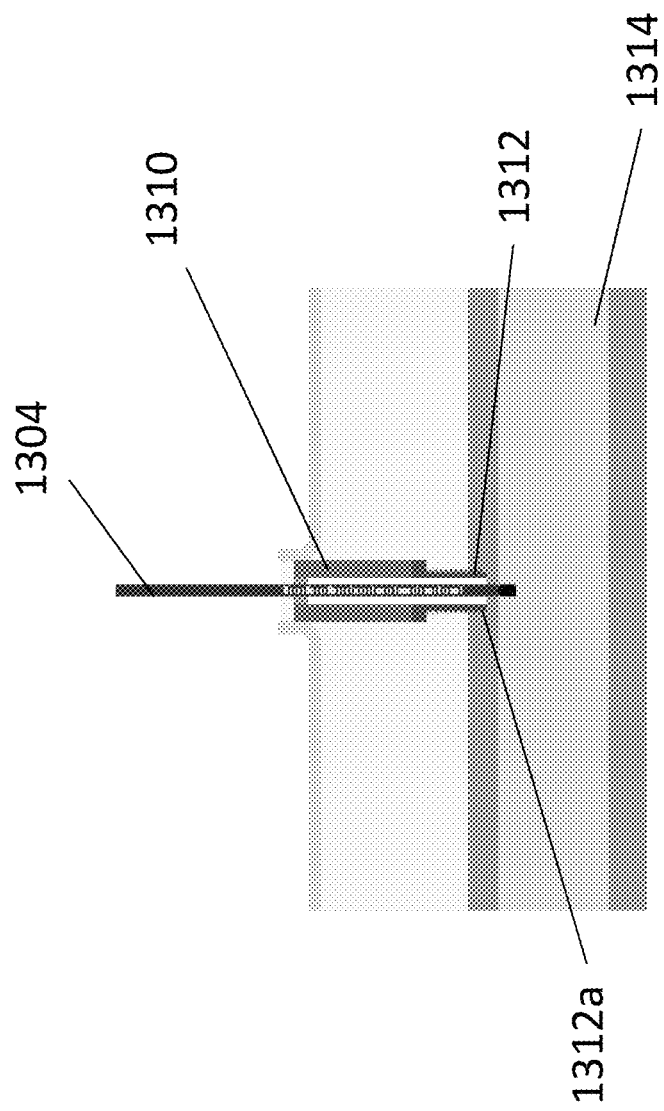
Figure 13E:
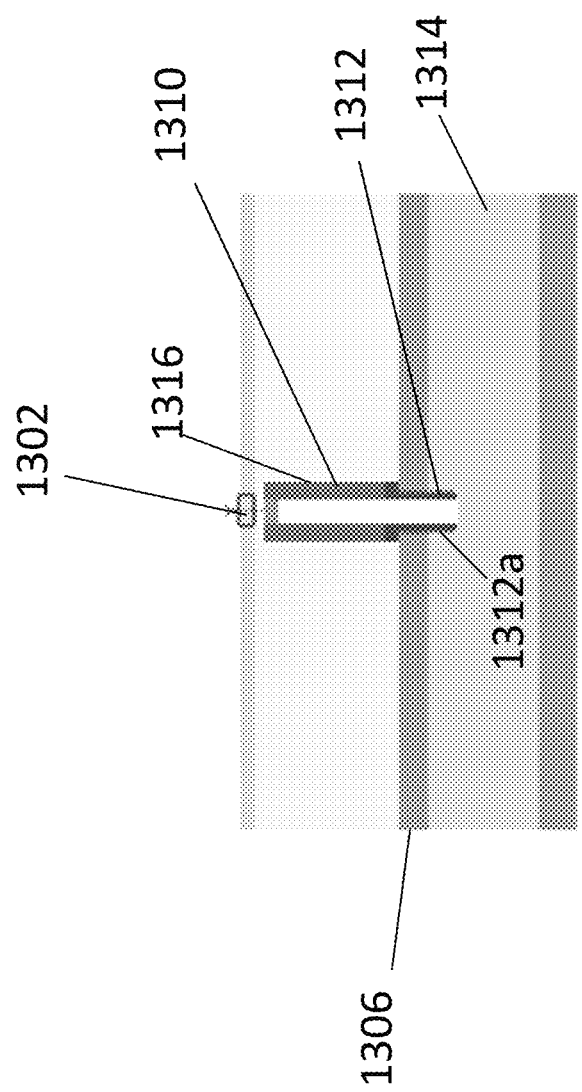

The device 1310 can then be passed through the incision 1302, over the guide wire 1304 if present, and bluntly through the soft-tissue layers 1308 until a distal portion 1312 of the device 1304 is in contact with the cortical surface of the bone 1306, as illustrated in FIG. 13D. Referring to FIG. 13E, the distal intraosseous portion 1312 of the device can then penetrate the bone 1306 and is advanced until a tip 1312a of the distal intraosseous portion 1312 lies in the marrow cavity 1314. Once fully implanted, the device 1310 can be anchored at the bone layer 1314, and the incision 1302 can be closed off with suture. In some embodiments, when the device is provided in components, the distal intraosseous portion 1312 may be inserted into the bone 1306 first and a proximal subcutaneous portion 1316 can be subsequently attached to the distal intraosseous portion 1312.

In some embodiments, after implantation, the IOP device 1310 may be temporarily accessed with a needle connected to a source of fluid. Fluids can be infused through the device 1310 to the marrow cavity 1314 to ensure good and adequate flow. If the flow is not adequate, the device 1310 may be advanced further into the marrow cavity 1314, withdrawn or repositioned. If it is still not adequate a different site on that bone or a different bone may be selected. Once the IOP device 1310 has been properly implanted underneath the skin, the stab incision 1302 may be closed with a suture or skin adhesive and dressed.

It should be appreciated that a fully assembled IOP device or its components may be provided in various sizes to accommodate different soft tissue and bone thicknesses. Specific models of IOP the device may be provided to target a specific bony location (e.g. clavicle, sternum, humerus) or specific type of marrow cavity (e.g. hollow vs. cancellous). In some embodiments, an IOP device kit may provide measuring devices to determine the soft tissue and/or bone thicknesses and allow the operator to select the appropriate size device or components of the device. The kit may also include specialized instruments to drive a distal intraosseous portion of the IOP device into a bone. The structure may include additional features to engage with such instruments. For example, if the anchoring mechanism includes screw like threads, the structure may resemble a bolt with a hexagonal head or other feature which allows the device to be screwed into place with an appropriate instrument. The device may be provided preloaded on such an instrument. The device may be provided with a guide wire which may be passed into the bone first. The device is then advanced over the guide wire. The guide wire may also serve as a measuring device to determine the soft tissue and/or bone thickness and allow the appropriate size device to be selected.

Figure 13F:
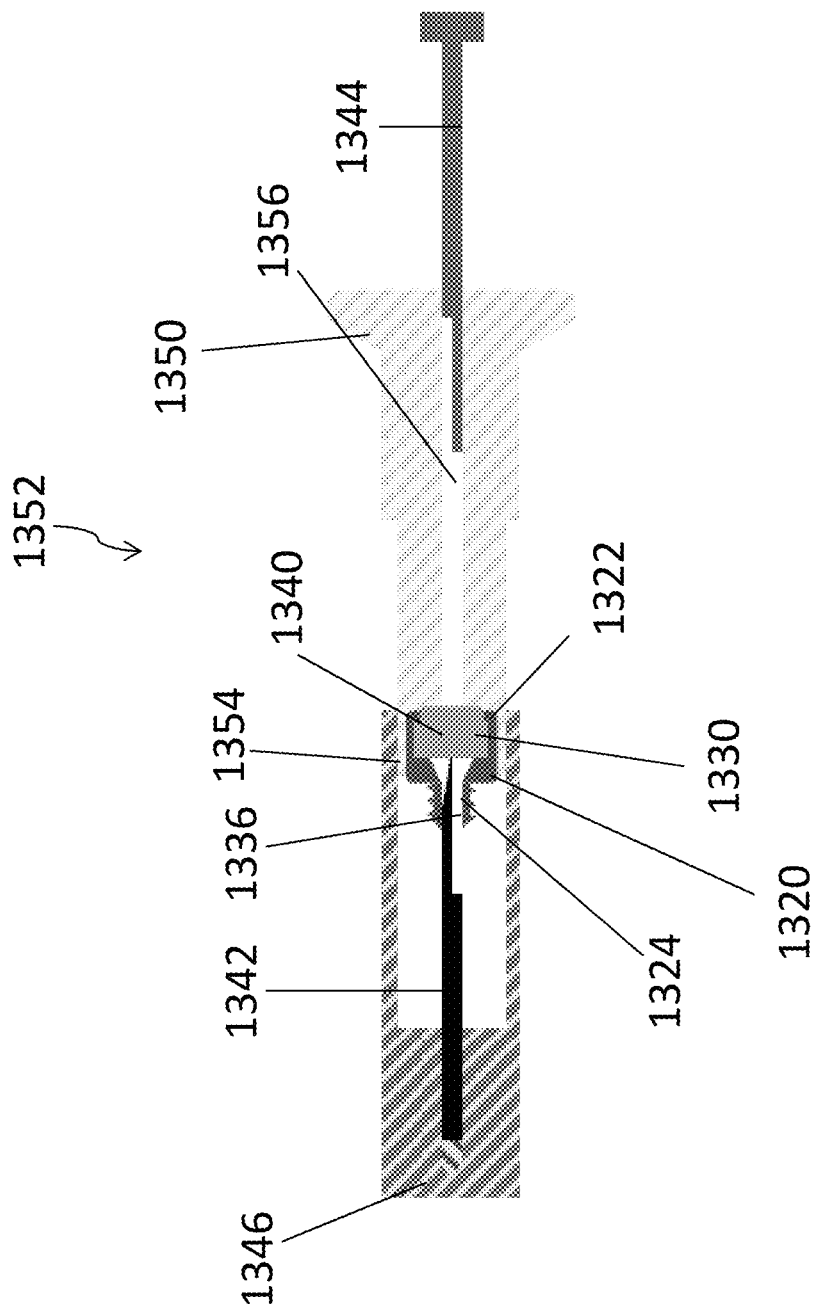

In some embodiments, an IOP device can be implanted into a bone using an implantation kit, as illustrated in FIGS. 13F-13P. Referring to FIG. 13F, a device implantation kit 1352 may include a driver 1350 for advancing the IOP device 1320 and a guide wire 1342 for guiding an IOP device 1320 into a desired location on the bone. As shown in FIG. 13F, the driver 1350 may securely hold the IOP device 1320 at a distal end 1354, where the hexagonal like portion of the IOP device 1320 can be complimentarily coupled to the distal end 1354. The inlet 1330 to the proximal portion 1322 on the IOP device 1320 may be covered by a septum 1340, and the guide wire 1342 can be aligned into the IOP device 1320 through the outlet 1336 of the distal portion 1324 so that the sharp proximal end of the guide wire 1342 is positioned to penetrate the septum 1340. The guide wire 1342 may be covered by a holder 1346, where the driver 1350 may be configured to slide into and out of the holder 1346. In addition, the driver 1350 may include a cannula 1356 for accommodating locking member such as a locking obturator 1344, where the obturator 1344 is designed to slide inside the cannula 1356.

Figure 13G:
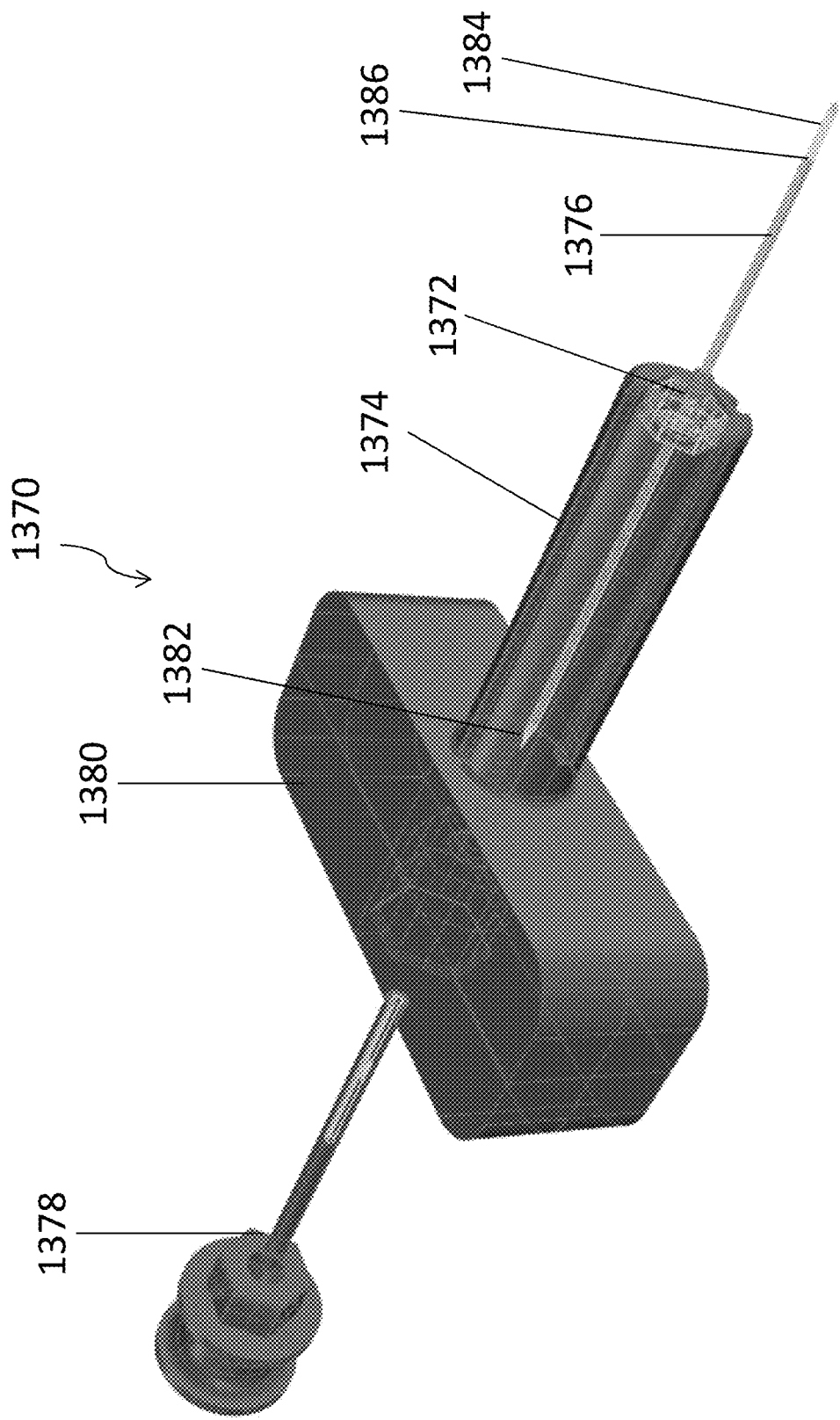

FIG. 13G illustrates a three dimensional view of a device implantation kit 1370 similar to the one presented in FIG. 13F. Referring to FIG. 13G, the kit 1370 can include an IOP device 1372 securely positioned at a distal end of a driver 1374, where a T-bar handle 1380 may provide gripping to an operator to drive the IOP device 1372 into a bone. The driver 1374 may be configured to advance the IOP device 1372 into a bone by applying a rotational force on the device 1372. In some embodiments, a guide wire 1376 may be used to guide the IOP device 1372 to a desired bone site. As shown in FIG. 13G, prior to implantation, a sharp proximal end of the guide wire 1382 can be inserted through the IOP device 1372 and through a septum covering the hollowed chamber of the IOP device 1372. An obturator 1378 is provided which can be inserted into the proximal portion of the driver 1374. With the obturator 1378 inserted, it engages the guide wire 1376 allowing the driver 1374 to drive the guide wire 1376 into the bone. With the obturator 1378 removed, the driver 1374 advances the IOP device 1372 over the guide wire 1376. In some embodiments, the guide wire 1376 may include a threaded distal portion 1384 designed to penetrate a bone's cortex layers, where the threaded portion 1384 can terminate at a ledge 1386 designed to function as a penetration stopping member to the threaded portion 1384.

Referring now to FIG. 13H and FIG. 13I, preparing the guide wire 1342 for insertion into a bone can include firstly penetrating the septum 1340 using a proximal tip 1358 of the guide wire 1342, which can be achieved by sliding the driver 1350 onto the guide wire, along with the IOP device 1320. Subsequently, as shown in FIG. 13I, the obturator 1344 can be pushed toward the guide wire 1342 along the cannula 1356, where a flat surface 1360 on the obturator 1344 can engage the proximal tip 1358 of the guide wire 1342. Subsequently, the holder 1346 can be removed, as shown in FIG. 13J to expose the guide wire 1342 for penetration into a bone.

Referring to FIG. 13K, before insertion into the bone, the implantation kit 1352 (minus the holder) may be positioned at an insertion site, where the skin may be numbed and a stab wound can be created. The implantation kit 1352 may then be inserted into the bone, where the guide wire 1342 may penetrate the bone, as shown in FIG. 13L. The obturator 1344 locks the guide wire 1342 so that rotation of driver 1350 rotates the guide wire 1342. Subsequently, the obturator 1344 may be removed, as shown in FIG. 13M, and the driver 1350 may advance the IOP device 1320 over the guide wire 1342 through the stab wound to reach the bone site. Once the IOP device 1320 is positioned at the bone site, the driver 1350 may advance the IOP device 1320 into the bone by applying a rotating force to the hexagonal proximal portion 1322 of the device 1320, as shown in FIG. 13N. When the IOP device 1320 is anchored into the bone 1348, the driver may be firstly removed (FIG. 13O), and the guide wire 1342 may be subsequently removed and the stab wound may be closed, as shown in FIG. 13P.

Figures 14A, 14B, 14C:
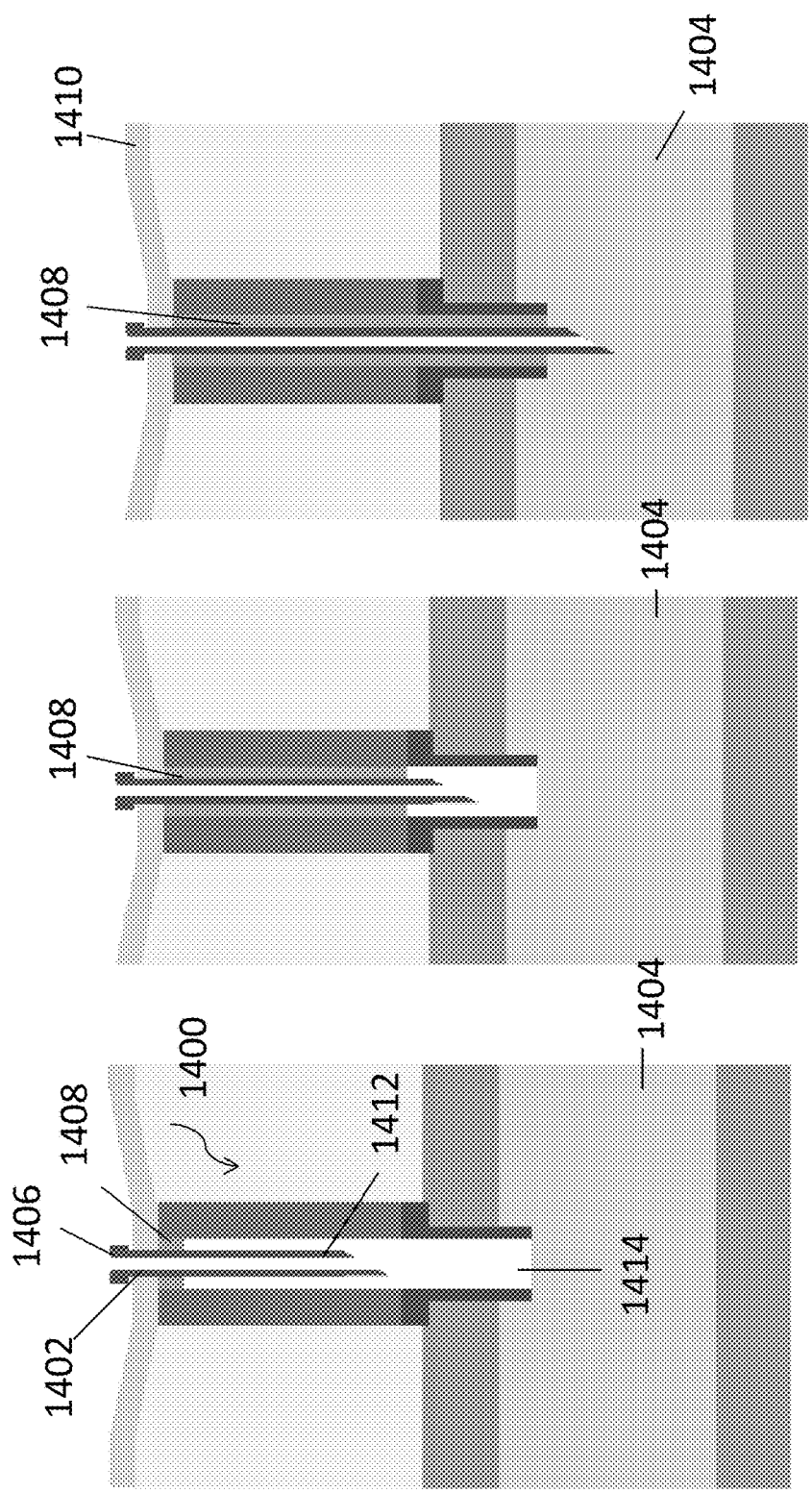
FIGS. 14A-14C illustrate IOP devices being accessed with different sized needles according to various embodiments of the present disclosure.

In some embodiments, an IOP device as described by the present disclosure may be used to infuse substances into a patient. Referring to FIGS. 14A-14C, a needle 1406 may be used to deliver fluids or medicines to and from a bone marrow cavity 1404. As illustrated in FIG. 14A, the IOP device 1400 may be submerged underneath a lay of skin 1410 covered by a septum 1408 designed to prevent reflux of the infused substance into the subcutaneous tissue. The needle 1406 can penetrate through the septum 1408 and into the hollow chamber 1412 and channel 1414 of the device 1400. Fluids and other substances can then be delivered through the needle 1406 and into the bone marrow cavity 1404. In some embodiment, a small volume of saline or other liquid can be infused into the hollow chamber 1412 and channel 1414 to ensure a proper positioning of the needle 1406. In some embodiments, the septum 1408 can extend partially or fully across the hollow chamber 1412 and channel 1414 of the device 1400. Correspondingly, the length of the needle 1406 can vary so the needle can reach different penetration depth within the device 1400 and the bone marrow cavity 1404. For example, referring to FIG. 14B, the needle 1406 can be of sufficient length such it can reach inside the channel 1414 of the IOP device 1400. In some embodiments, the needle 1406 may be long enough such a tip of the needle can go into the bone marrow cavity 1404, as illustrated in FIG. 14C. As such, the needle 1410 can easily penetrate through material buildups or clogs within the device 1400 to ensure a good flow into the marrow cavity 1404. Moreover, for configurations where an IOP device has no hollow chambers, a needle can also go into the marrow cavity 1404.

One advantage offered by the IOP devices presented by the present disclosure is that the IOP devices do not come into contact with free flowing blood. As such, unlike traditional VADs, no draw back to confirm blood return through the needle is needed.

Figure 15A:
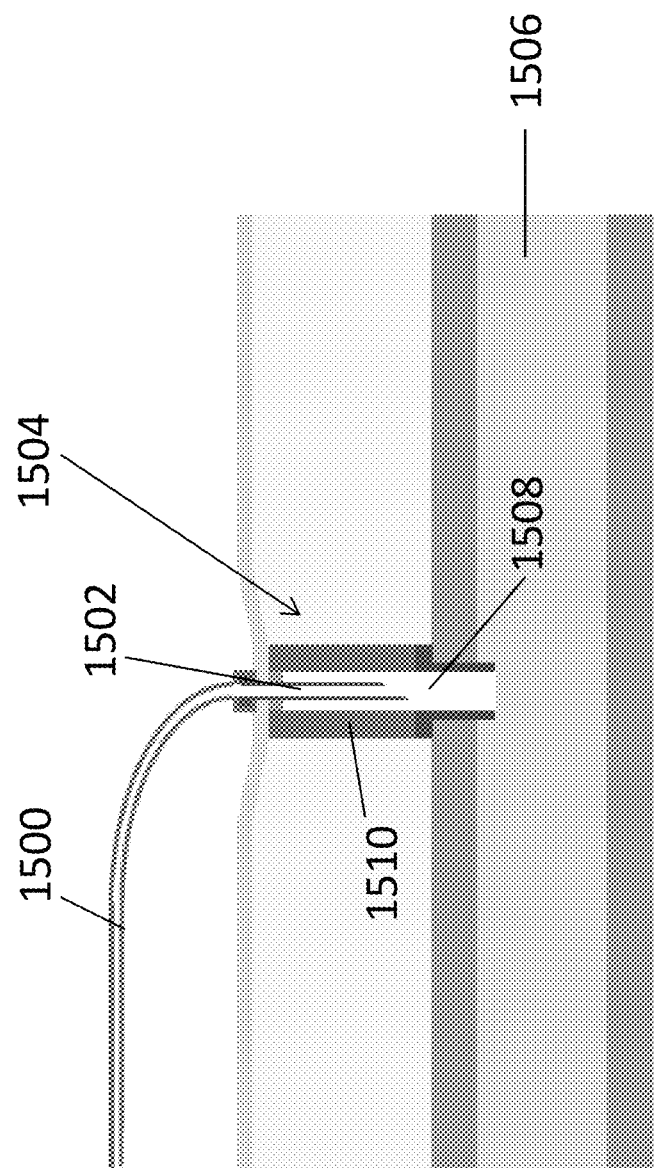
FIG. 15A illustrates a single structured IOP device being accessed with a needle according to various embodiments of the present disclosure.
Figure 15B:
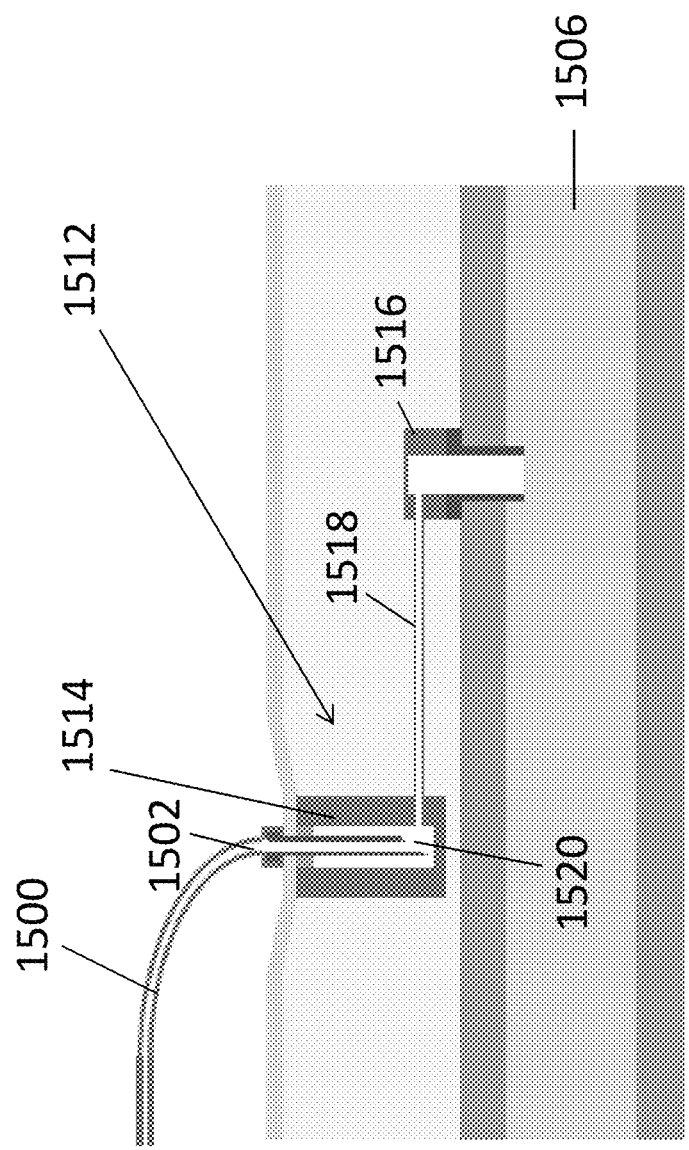
FIG. 15B illustrates a multi-bodied IOP device being accessed with a needle according to various embodiments of the present disclosure.

Furthermore, in some embodiments, a needle may be connected to containers (bag, syringe, etc.) containing substances that are to be infused into the bone marrow. Referring to FIG. 15A and FIG. 15B, a needle 1502 may be connected to a tube 1500 for delivering fluids to a bone marrow cavity 1506. When a single structured IOP device 1504 is being used for accessing the bone marrow 1506, as shown in FIG. 15A, the needle 1502 may go directly into a hollow chamber 1508 disposed within a proximal portion 1510 of the IOP device 1504. Referring now to FIG. 15B, where a multi-bodied IOP device 1512 may be used for accessing the bone marrow 1506. The IOP device 1512 may include a proximal portion 1514 positioned away from the distal portion 1516, where the proximal 1514 and distal 1516 portions may be connected by a tube 1518. In this configuration, the needle 1502 can be inserted to a hollow chamber 1520 of the proximal portion 1514, and fluids can be delivered to and from the distal portion 1516 through the connecting tube 1518.

Figure 16B:
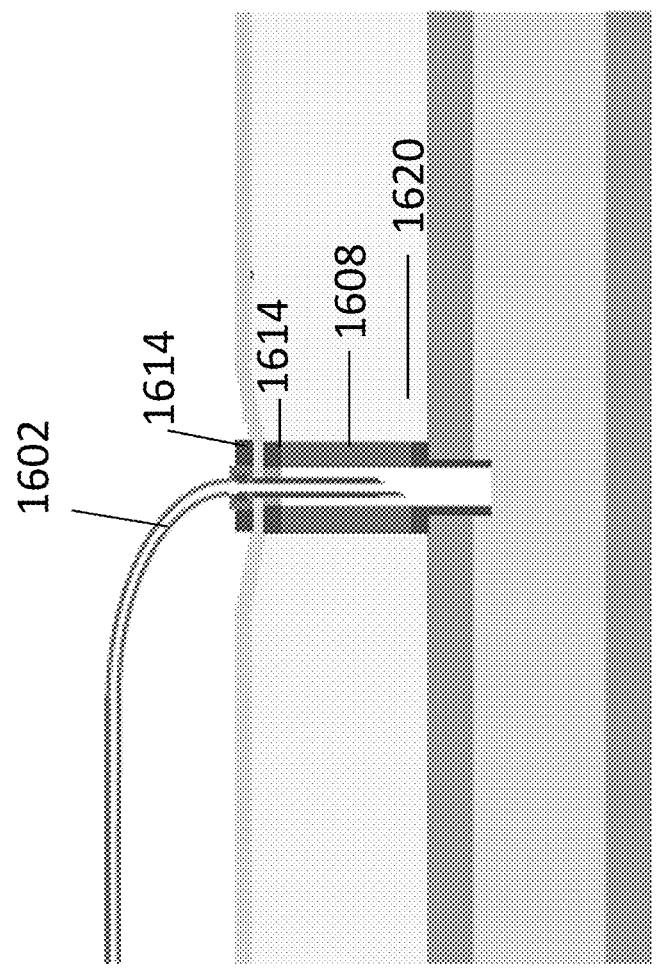

To better assist a proper positioning of the needle, several measures can be utilized, as illustrated in FIG. 16A and FIG. 16B. Referring to FIG. 16A, a proximal portion 1606 of an IOP device 1610 can have a funnel like shaped hollow chamber 1604 with sloped walls. The sloped walls can in turn help guiding the needle 1602 towards the center of the hollowed chamber 1604 and into a distal portion 1612 of the IOP device 1610. In some embodiments, apparatuses such as magnetic rings can be coupled to the needle 1602 and a proximal portion 1608 of an IOP device 1620, for guiding the needle 1602. Referring to FIG. 16B, a magnetic ring 1614 can be coupled to a proximal end of the proximal portion 1608, and a similar magnetic ring 1614 can be couple to the needle 1602. When the needle is inserted into the proximal portion 1608, the magnetic forces of the rings 1614 can guide the needle towards the center of the proximal portion 1608.

The IOP devices presented by the present disclosure may be deployed for numerous medical applications, for example, an IOP device, either in a single structured configuration or a multi-bodied configuration can be utilized as Arterio-Osseous Ports for Hemodialysis applications. Currently a majority of patients with dialysis-dependent renal disease undergo hemodialysis. Hemodialysis requires a site to draw blood from the patient and another site to re-infuse the dialyzed blood back into the patient. There are several options available to the patients and their clinicians. A temporary or long-term (tunneled) dialysis catheter may be inserted into a central vein. It has at least two lumens which terminate near or within the right atrium with inlet and outlet ports separated by a certain distance to minimize recirculation of dialyzed blood. Alternatively, an arterio-venous fistula can be surgically created by attaching a peripheral vein to a peripheral artery. This engorges the vein and provides enough flow to efficiently dialyze the patient. The fistula may be native, with a direct connection between the artery and vein, or a prosthetic graft may be inserted between the artery and vein. These options have several disadvantages including the risk of infection, thrombosis, etc. Most importantly, accessed veins can fibrose and stenose and eventually occlude. It is not uncommon for long-term dialysis patients to "run out" of venous access sites after years of dialysis.

An arterio-osseous fistula device can create a communication between an artery and the marrow cavity of a bone. FIGS. 17A-17C, FIG. 18A and FIG. 18B, and FIG. 19-23 are diagrams illustrating IOP devices as presented by the present disclosure being used as arterio-osseous fistulas suitable for hemodialysis accesses. In some embodiments, arterio-osseous fistulas (AOF) are implantable infusion devices that allow liquid substances, such as dialyzed blood, to be infused into the marrow cavity of a bony structure. At the same time, an AOF device can be connected to an artery allowing blood to be withdrawn from the patient as well. An AOF device can consists of two parts which can be considered separate ports, a first—"arterial"—port, and a second—"venous"—port.

In some embodiments, an AOF infusion system may include a first port having a chamber from which fluids can be withdrawn, and a second port having a cavity in fluid communication with the chamber from the first port, the second port being designed to receive an insertion device. The infusion system may further include an anchor portion extending distally from the second port for secured placement into a bone, the anchor portion having a channel extending from the cavity through the anchor portion and terminating in an opening so as to provide a substantially straight pathway from the cavity and through which an insertion device can be directed towards the bone marrow. In some embodiments, the first port may further include an inlet coupled to an artery for withdrawing fluids.

Figure 17A:
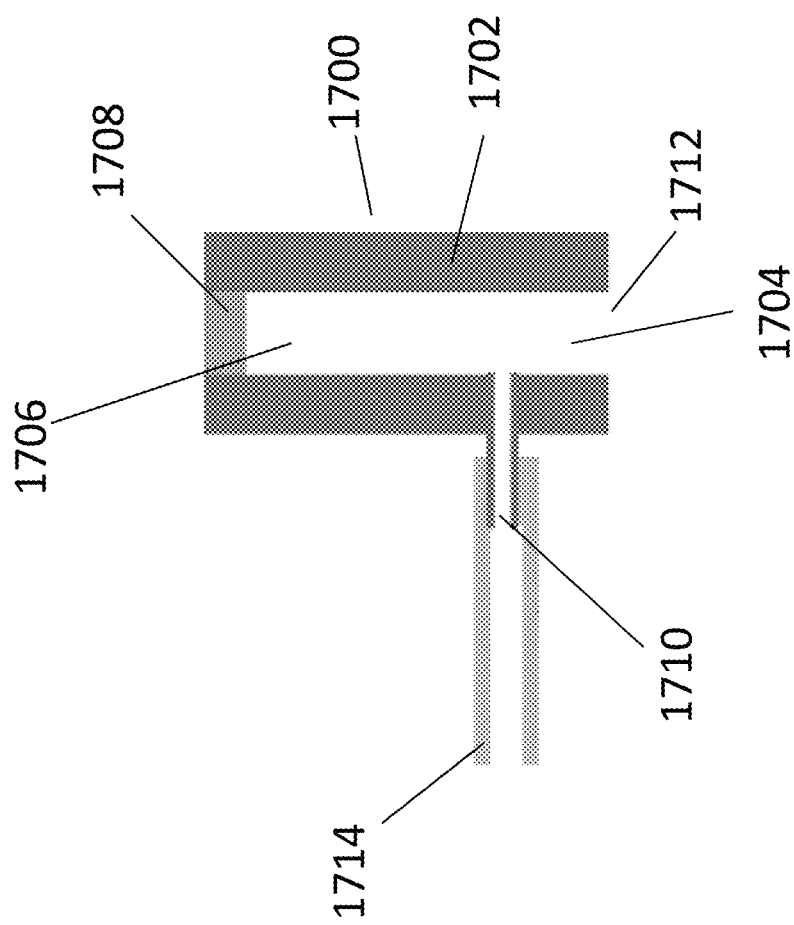
FIGS. 17A-17C illustrate arterial connection configurations for Arterio-Osseous Ports according to various embodiments of the present disclosure.
Figure 17B:
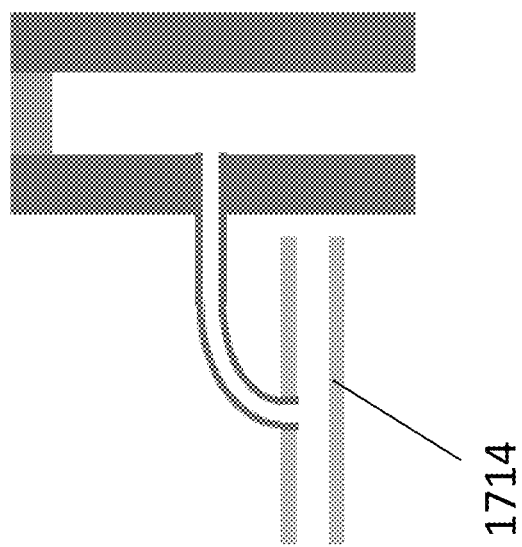
Figure 17C:
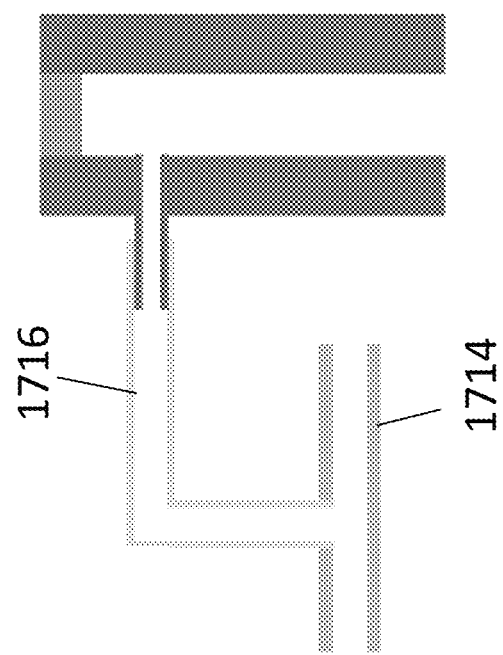

The arterial port, from which the dialysis machine withdraws blood to be dialyzed, consists of a separate subcutaneous port accessible through the skin. Any of the embodiments of the proximal subcutaneous portion of the IOP devices described above may be suitable for the arterial port. Referring to FIGS. 17A-17C, an arterial port 1700 may include a body 1702, a hollow chamber 1704, which may be a channel or a reservoir, an access site 1706 with a septum 1708, an arterial inlet 1710 and an outlet 1712, where the arterial inlet 1710 may connect the arterial port 1700 to an artery 1714. The artery 1714 may connect directly to the port in an end-to-side configuration as shown in FIG. 17A, or a side-to-side configuration as shown in FIG. 17B. In some embodiments, as illustrated in FIG. 17C, the arterial port 1700 may be connected to the artery 1714 through a native (e.g. saphenous vein) or prosthetic conduit 1716. In some embodiments, the arterial and/or venous ports may serve as conduits themselves. For example, at least a portion of the conduit may lie superficially in a subcutaneous tissue so that the arterial and/or venous lines from the dialysis machine may access it.

The venous port, which receives the dialyzed blood from a dialysis machine, can be functionally identical to an IOP device with a proximal subcutaneous portion accessible through the skin and a distal intraosseous portion which traverses the bone's cortex into the bone marrow cavity. In some embodiments, the venous port may include a cavity (similar to the hollow chamber in an IOP device presented in the present disclosure) in fluid communication with the chamber 1704 from the arterial port. The venous port may be designed to receive an insertion device and have an anchor portion extending distally from the cavity for secured placement into a bone. In some embodiments, the anchor portion may have a channel extending from the cavity of the venous port through the anchor portion and terminating in an opening so as to provide a substantially straight pathway from the cavity and through which an insertion device can exit and be directed into the bone. It should be appreciated that any of the IOP embodiments described above may be suitable for the venous port of the AOP.

In order to prevent thrombosis, the arterial port may need continuous fluid flow, meaning that the arterial port's outlet must be in fluid communication with the marrow cavity. The specific pathway for this communication depends on the relationship between the arterial and venous ports. The port design and the artery utilized assure that the flow through the port will be adequate to prevent thrombosis. Adjunctive measures may be added including the administration of anti-platelet or anti-coagulant agent and/or coating all blood contact surfaces with heparin or other anti-thrombotic coating.

Figure 18A:
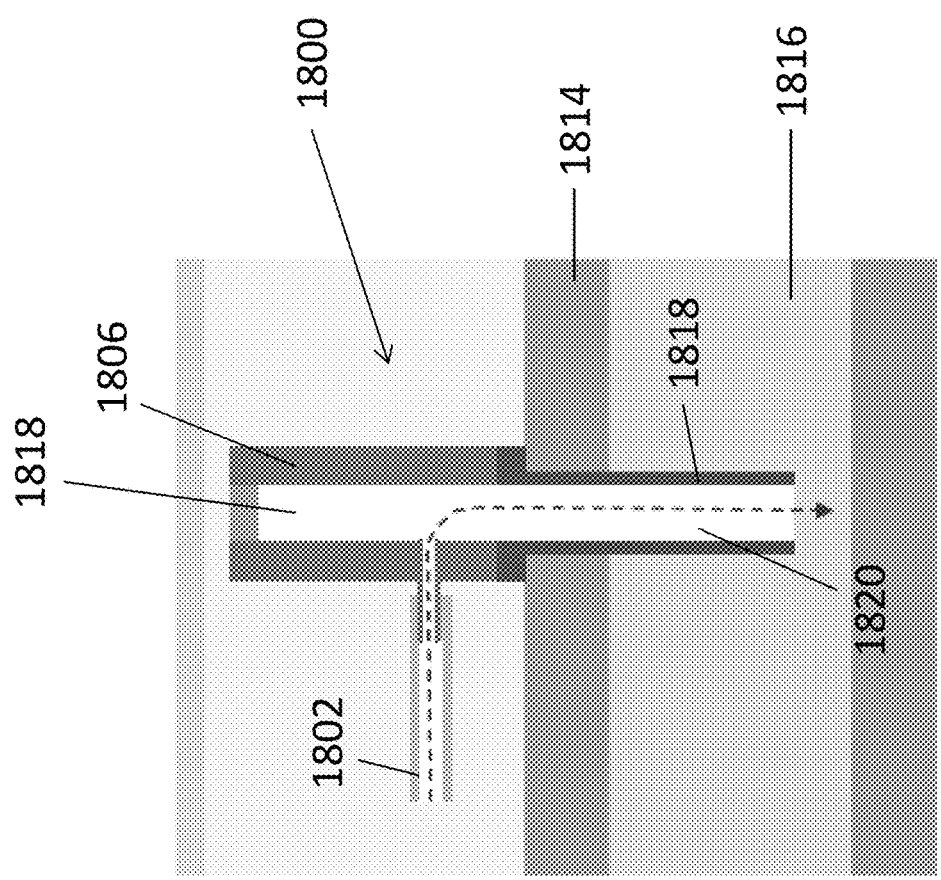
FIG. 18A and FIG. 18B illustrate Arterial and Venous Ports for Arterio-Osseous Ports according to various embodiments of the present disclosure.
Figure 18B:
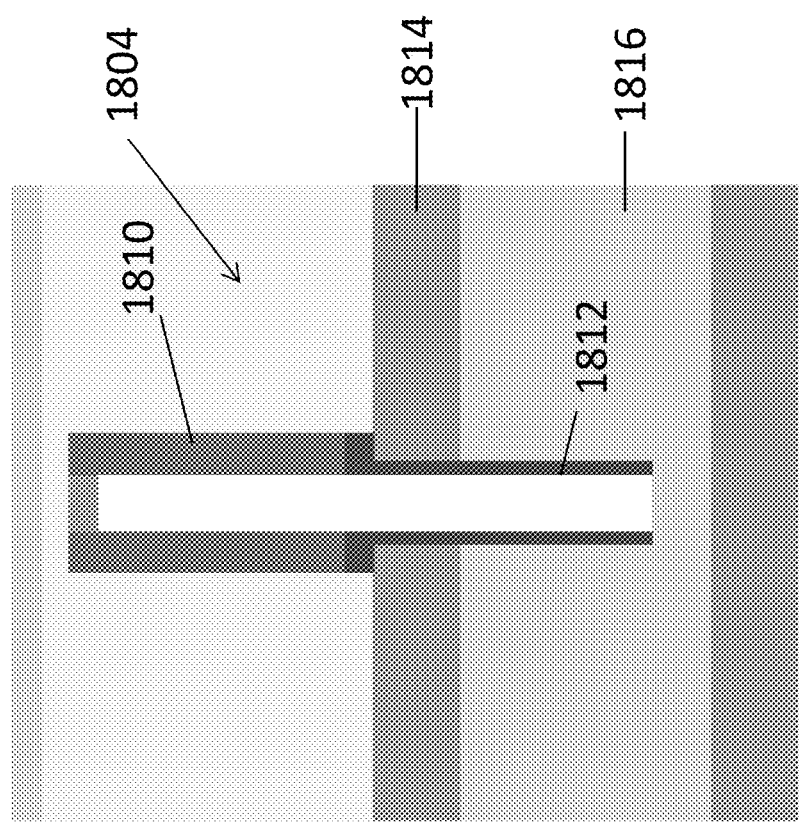
Figure 19:
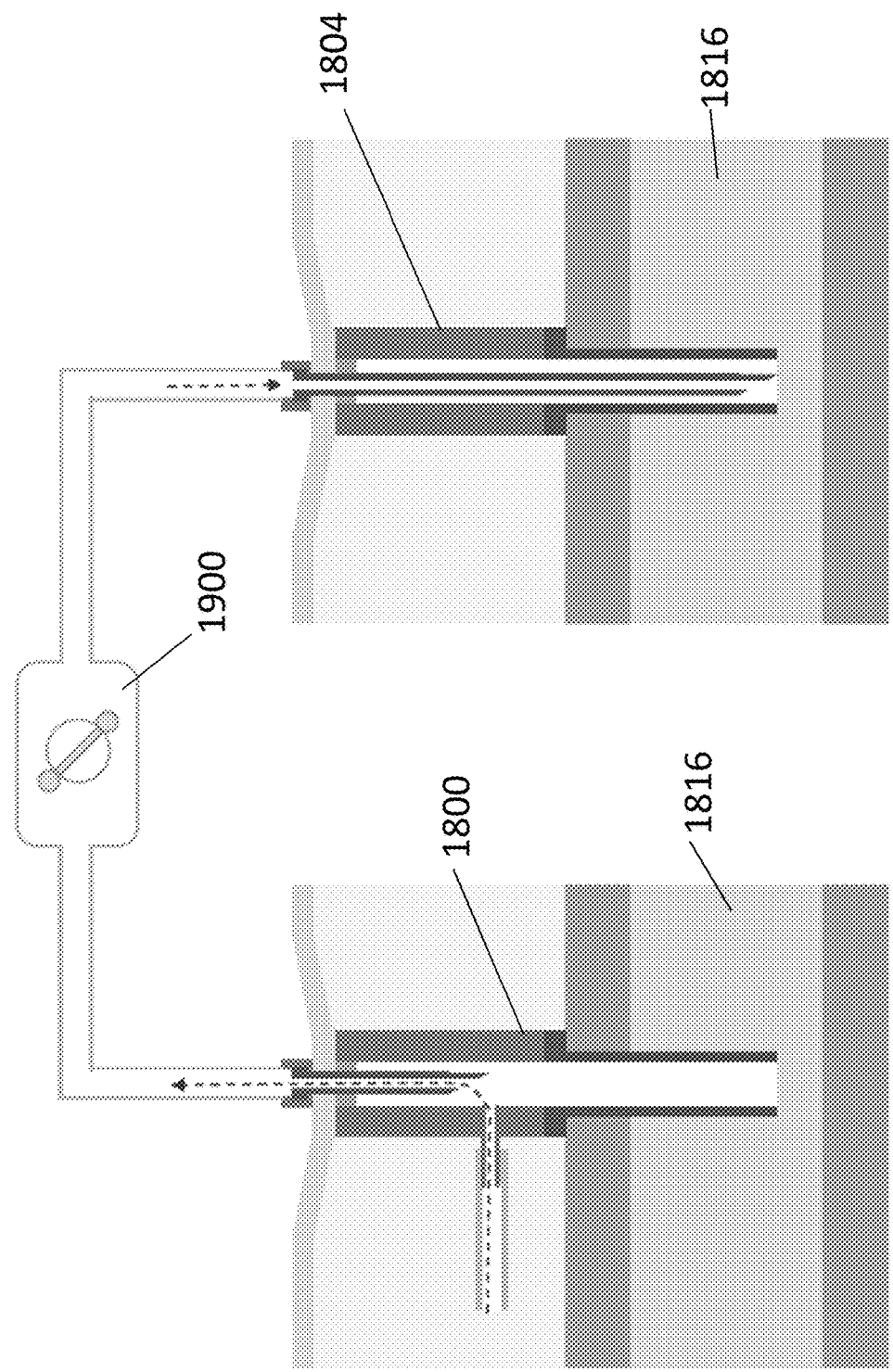
FIG. 19 illustrates separate Arterial and Venous Ports for Dialysis applications according to various embodiments of the present disclosure.

In some embodiments, an arterial port and a venous port may be structurally and functionally separate, as illustrated in FIGS. 18A-18B, and FIG. 19. Referring to FIG. 18A, an arterial port 1800 may be an IOP device with a connection to an artery 1802 creating an arterio-osseous fistula (AOF). Similarly, as illustrated in FIG. 18B, a venous port 1804 may be an IOP device through which dialyzed blood can be re-infused back into the patient. Like IOP devices presented in the present disclosure, both the arterial port 1800 and the venous port 1804 may have a proximal subcutaneous portion 1806, 1810 accessible through the skin and a distal intraosseous portion 1808, 1812 which passes through the cortex 1814 of the bone into the marrow cavity 1816. When the arterial 1800 and venous 1804 ports are not being accessed for a dialysis treatment, arterial blood flowing through a hollow chamber 1818 and a hollow channel 1820 of the arterial port 1800 and into the marrow cavity 1816. When arterial blood is being process by a dialysis machine 1900 as illustrated in FIG. 19, the arterial blood can be actively drawn from the patient through the arterial port 1800 firstly into the dialysis machine 1900 and then returned through the venous port 1804 and into the patient's marrow cavity 1816.

Figure 20:
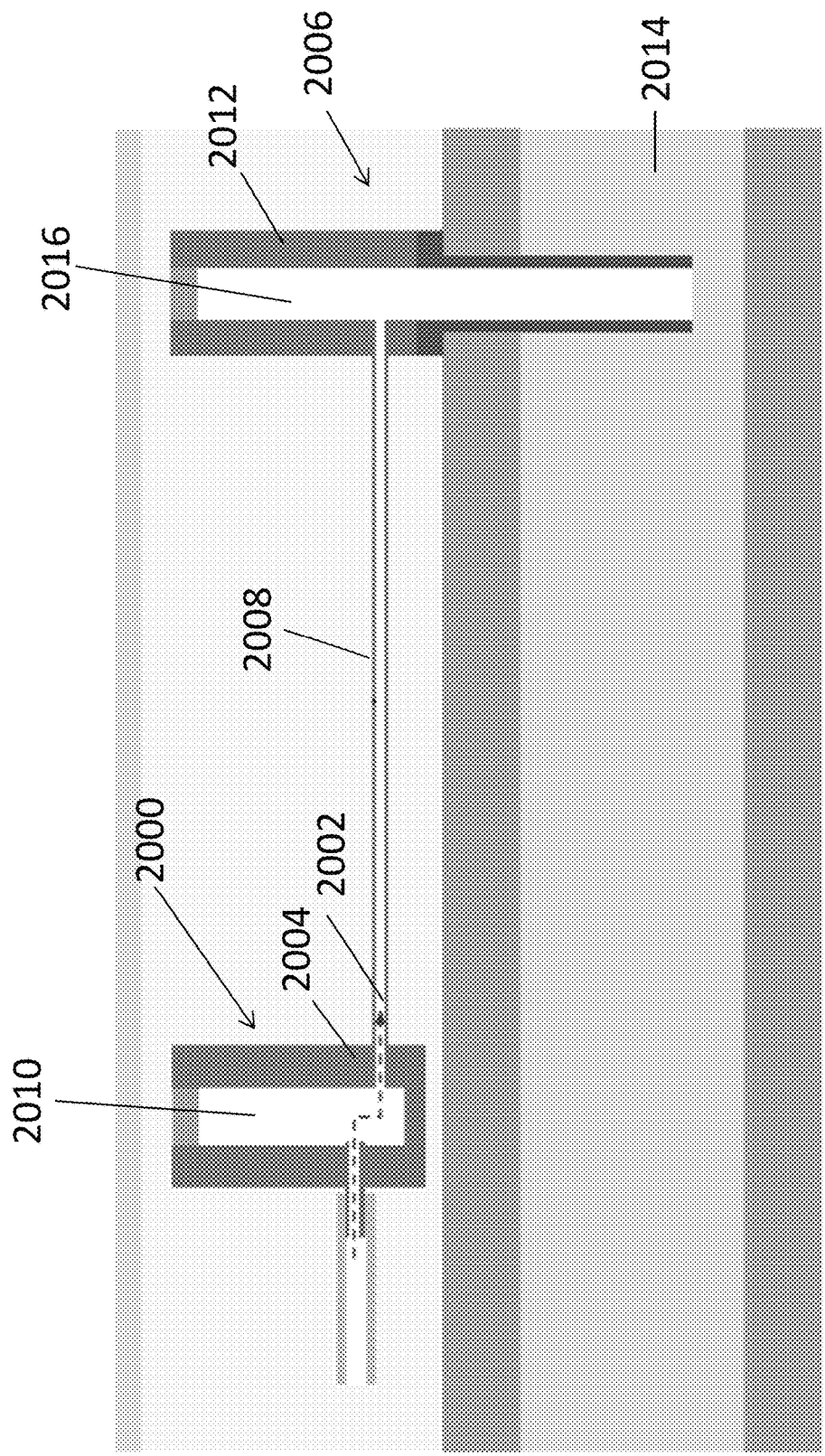
FIG. 20 illustrates structurally separate Arterial and Venous ports being linked functionally according to various embodiments of the present disclosure.
Figure 21:
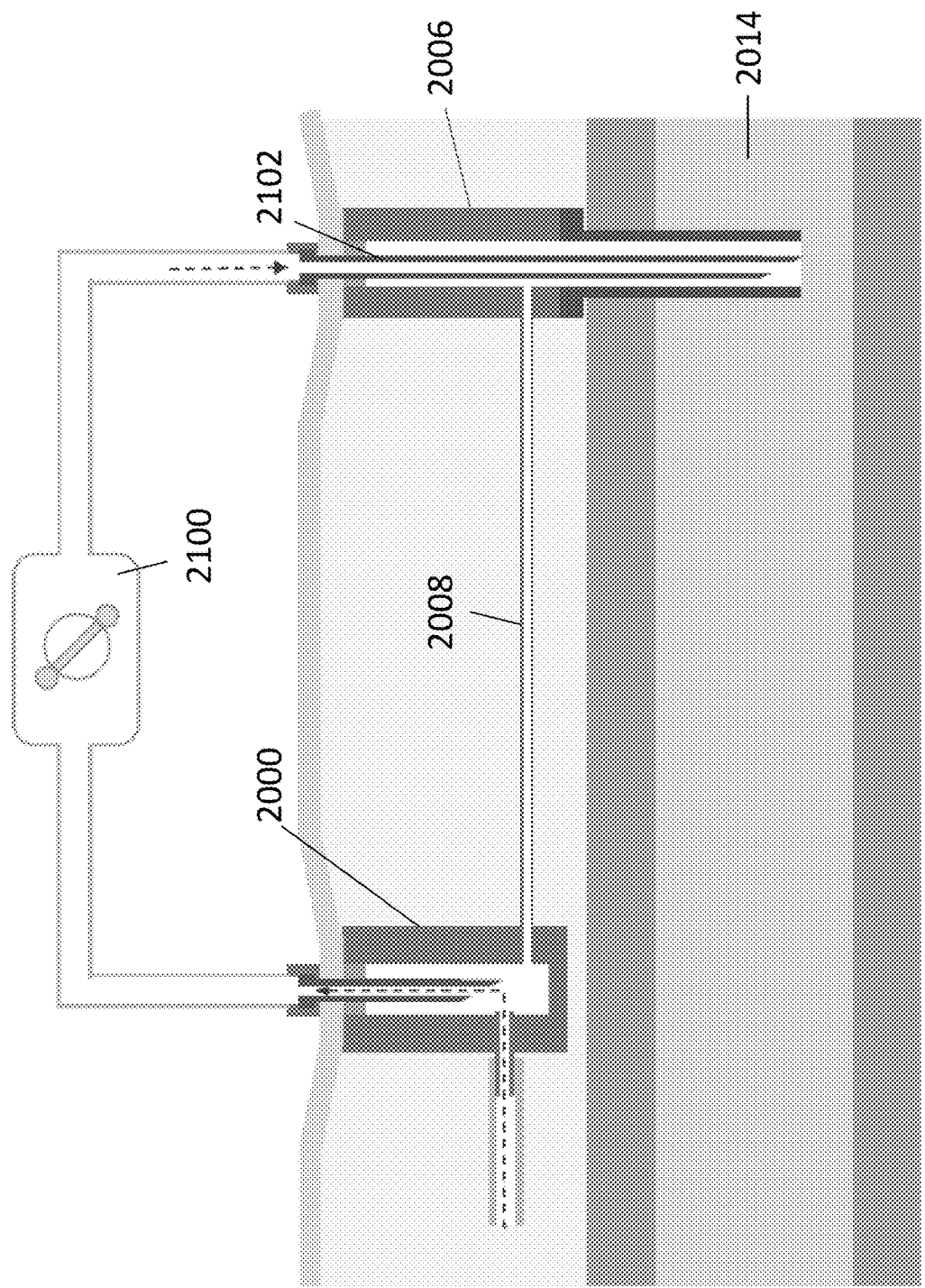
FIG. 21 illustrates structurally separate Arterial and Venous ports being used for dialysis applications according to various embodiments of the present disclosure.

In some embodiments, the arterial and venous ports may remain structurally separate but functionally linked, as illustrated in FIG. 20 and FIG. 21. As shown in FIG. 20, an arterial port 2000 does not necessarily have to possess a dedicated intraosseous portion but only a subcutaneous portion 2004. Instead, an outlet 2002 of the subcutaneous portion 2004 can communicate with a venous port 2006 through a catheter, connecting tubing, graft 2008, or any suitable apparatus capable of creating a passageway between the arterial 2000 and venous 2006 ports, where the venous port 2006 may include a cavity 2016 in fluid communication with the marrow cavity 2014. When not being accessed for a dialysis treatment, arterial blood may flow through a hollow chamber or cavity 2010 of the arterial port's 2000 subcutaneous portion 2004, through the catheter 2008, through a subcutaneous intraosseous portion 2012 of the venous port 2006 and finally into the marrow cavity 2014. Referring to FIG. 21, when arterial blood is being processed by a dialysis machine 2100, arterial blood can be actively drawn from the patient through the arterial port 2000 and into the dialysis machine 2100. After the dialysis machine 2100 has processed the arterial blood, the arterial blood can be returned to the patient's marrow cavity 2014 through the venous port 2006. Recirculation of the dialyzed blood through the catheter 2008 can be avoided in several ways. Firstly, the diameter of the catheter 2008 may be made small enough that it provides enough resistance to favor flow into the marrow 2014. Alternatively, a valve may be interposed to assure unidirectional flow through the catheter. Finally, as shown in FIG. 20, a needle 2102 in the venous port 2006 may be inserted well into the intraosseous portion or even into the marrow 2014, obstructing the orifice of the catheter 2008.

Figure 22:
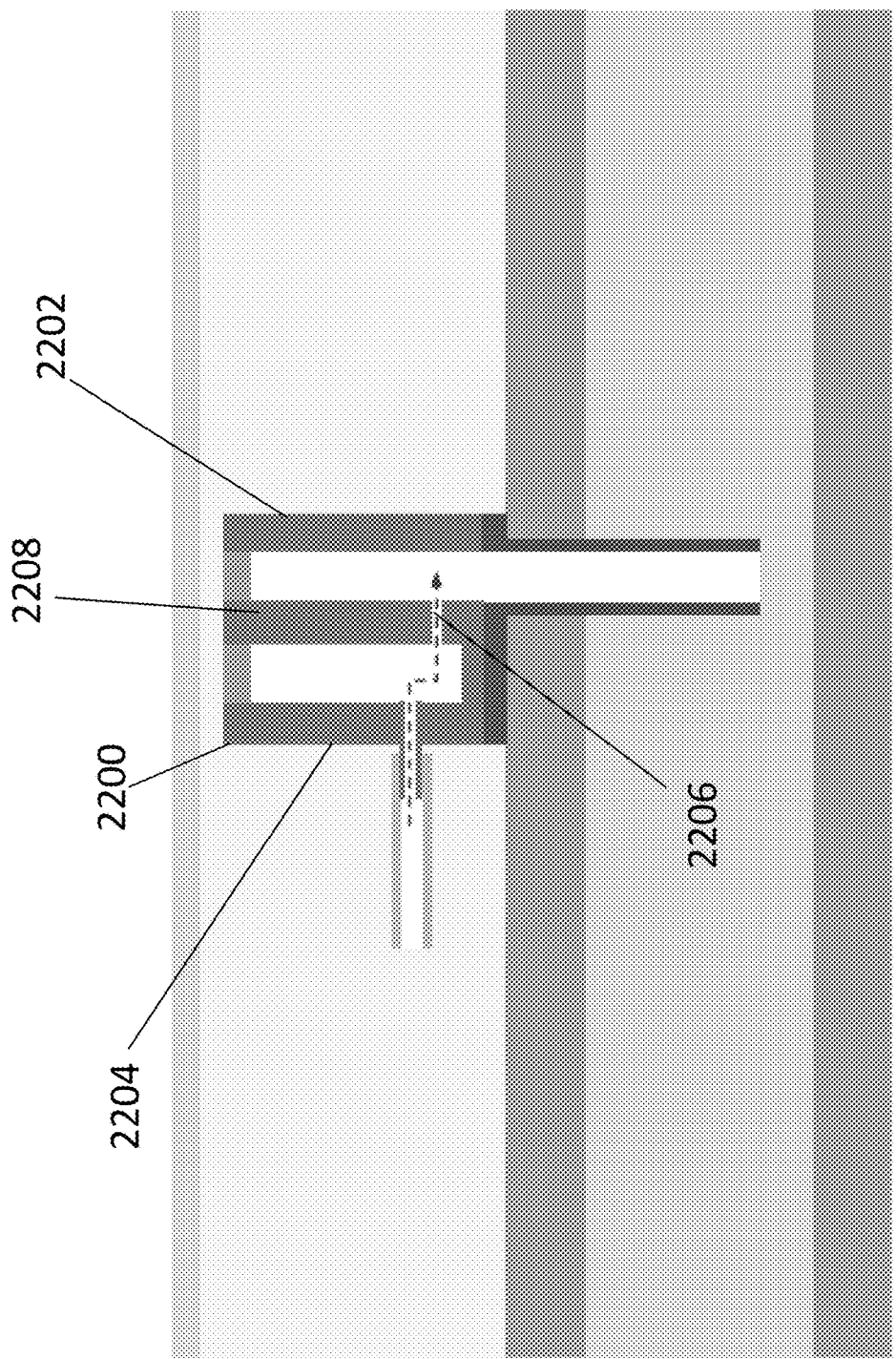
FIG. 22 illustrates structurally linked Arterial and Venous ports according to various embodiments of the present disclosure.
Figure 23:
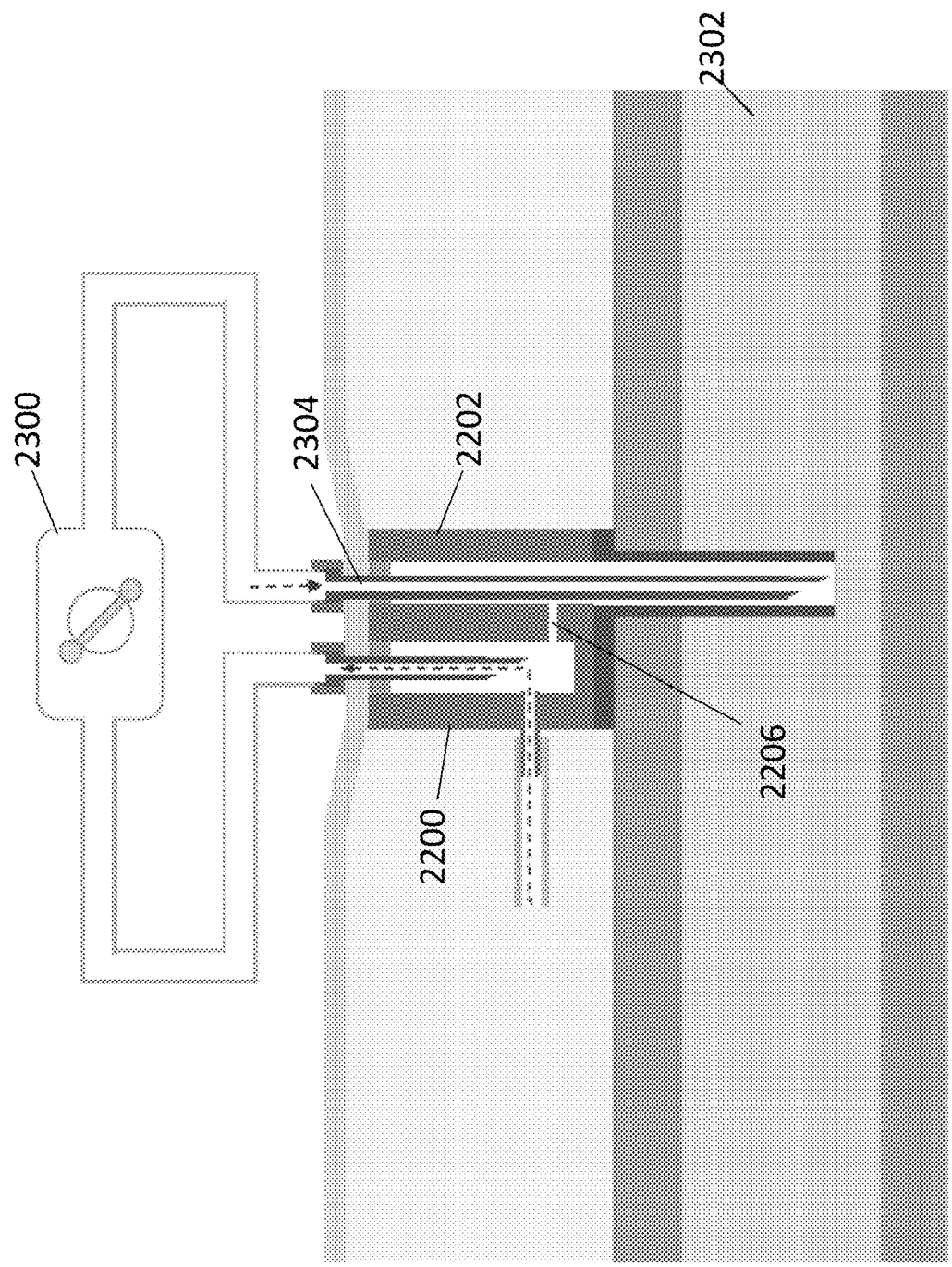
FIG. 23 illustrates structurally linked Arterial and Venous ports being used for dialysis applications according to various embodiments of the present disclosure.

In some embodiments, an arterial port and a venous port can be structurally and functionally linked for various medical applications, as illustrated in FIG. 22 and FIG. 23. As shown in FIG. 22, an arterial port 2200 with only a subcutaneous portion 2204 can be structurally linked with a venous port 2202. The arterial port 2200 can be placed side by side with the venous port 2202, where fluidic communication between the arterial 2200 and venous 2202 ports can be accomplished through an internal channel 2206. In some embodiments, the arterial 2200 and venous port 2202 can be structurally linked such that the two ports share a common sidewall 2208, as illustrated in FIG. 22. The internal channel 2206 can pass through the common sidewall 2208 to provide a path for delivering fluids and substances between the arterial 2200 and venous 2202 ports. When used for dialysis applications, referring to FIG. 23, arterial blood can be actively drawn from the patient through the arterial port 2200 and into a dialysis machine 2300. After the dialysis machine 2300 has processed the arterial blood, arterial blood can be returned to the patient's marrow cavity 2302 through the venous port 2202. In some embodiments, as shown in FIG. 23, a needle 2304 in the venous port 2202 may be inserted well into the intraosseous portion or even into the marrow 2302, preventing recirculation of venous or arterial blood through the internal channel 2206.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A method for operating an infusion device comprising:
   introducing an infusion device to a bone site, the infusion device comprising:
      a chamber having sloped walls and a proximal inlet for receiving an insertion device;
      an anchor portion being in fluid communication with the chamber and having a channel extending from a proximal end of the anchor portion and and terminating at an opening at a distal end of the anchor portion; and
      a flat surface substantially perpendicular to the anchor portion at a junction between the chamber and the anchor portion;
   advancing the anchor portion into a bone and toward bone marrow until the proximal inlet of the chamber is subcutaneous and the flat surface contacts the bone to limit a depth of penetration into the bone by the anchor portion, to provide a substantially straight pathway from the chamber through the anchor portion for direct access to the bone marrow; and
   allowing the sloped walls of the chamber to direct an insertion device into the substantially straight pathway.

2. The method of claim 1, wherein the step of introducing the infusion device comprises using a guide wire to guide the infusion device to the bone site.

3. The method of claim 1, wherein the step of advancing the anchor portion comprises applying a rotating force to the infusion device.

4. The method of claim 1, wherein:
   the chamber includes a magnetic ring positioned about the proximal inlet; and
   allowing the magnetic ring to guide the insertion device into the opening.

5. A method for operating an infusion device comprising:
   advancing over a guidewire an infusion device to a site of interest, the infusion device having a chamber, an anchor portion, and a flat surface substantially perpendicular to the anchor portion and located at a junction between the chamber and the anchor portion, the chamber having a proximal inlet for receiving an insertion device, the anchor portion having a proximal end, a distal end, and a channel therebetween, the channel extending along a length of the anchor portion, terminating at an opening, and being in fluid communication with the chamber;
   manipulating the proximal inlet of the chamber from the site of interest to a second subcutaneous position;
   advancing the anchor portion toward bone marrow until the flat surface contacts the bone to limit a depth of penetration into the bone by the anchor portion, such that, a pathway between the anchor portion and the proximal inlet provides the insertion device with direct access to the bone marrow; and
   inserting the insertion device through the pathway and toward the bone marrow, wherein the chamber includes sloped walls configured for guiding an insertion device into the pathway of the anchor portion.

6. The method of claim 5, wherein the step of advancing the anchor portion comprises applying a rotating force to the infusion device.

7. The method of claim 5, wherein:
   the chamber includes a magnetic ring positioned about the proximal inlet; and
   the inserting the insertion device includes allowing the magnetic ring to guide the insertion device into the opening.

8. A method for operating an infusion device comprising:
   providing an infusion device, the infusion device comprising:
      a chamber having a proximal inlet configured for subcutaneous placement and receiving an insertion device;
      an anchor portion having a proximal end, a distal end, and a channel terminating at an opening at the distal end of the anchor portion, and being in fluid communication with the chamber; and
      a flat surface substantially located at a junction between the chamber and the anchor portion, extending perpendicular to the anchor portion, and designed to limit a depth of penetration into the bone by the anchor portion; and
   inserting the infusion device through an incision until a distal portion of the anchor portion engages a bone;
   rotating the infusion device to advance the anchor portion into the bone toward a bone marrow cavity in a self-tapping and self-drilling operation, such that, when the infusion device is implanted into the bone, the channel provides the insertion device with direct access to the bone marrow; and
   inserting the insertion device through the pathway and toward the bone marrow, wherein the chamber includes sloped walls configured for guiding an insertion device into the channel of the anchor portion.

9. The method of claim 8, wherein the step of providing the infusion device comprises using a guide wire to guide the infusion device to the bone site.

10. The method of claim 8, wherein:
    the chamber includes a magnetic ring positioned about the proximal inlet; and
    the step of inserting the insertion device includes allowing the magnetic ring to guide the insertion device into the channel.

11. A method for operating an infusion device comprising:
    providing an infusion device having:
       an anchor portion having a channel extending along its entire length and terminating at an opening;
       a chamber having an inlet at one end and being in fluid communication, at an opposing end, with the anchor portion, the chamber configured for subcutaneous placement and having sloped walls for guiding an insertion device into the channel; and
       a flat surface, substantially perpendicular to the anchor portion, located at a junction between the chamber and the anchor portion;
    advancing the infusion device until the inlet of the chamber is subcutaneous and the flat surface contacts a bone; and
    allowing the flat surface to limit depth of penetration of the infusion device into the bone, such that the channel provides direct access to bone marrow from the chamber.

* * * * *